(12) United States Patent
Palushi et al.

(10) Patent No.: US 11,890,026 B2
(45) Date of Patent: Feb. 6, 2024

(54) MEDICAL INSTRUMENT WITH INTEGRAL NAVIGATION CONTROL FEATURES

(71) Applicants: Acclarent, Inc., Irvine, CA (US); Biosense Webster (Israel) Ltd., Yokneam (IL)

(72) Inventors: Jetmir Palushi, Irvine, CA (US); Itzhak Fang, Irvine, CA (US); Ehsan Shameli, Irvine, CA (US); David A. Smith, Jr., Lake Forest, CA (US); Fatemeh Akbarian, Rancho Palos Verdes, CA (US); Henry F. Salazar, Pico Rivera, CA (US); John H. Thinnes, Jr., Mission Viejo, CA (US); Hany Abdelwahed, Irvine, CA (US); Babak Ebrahimi, Irvine, CA (US); Oleg Dulger, Yoqneam Ilit (IL)

(73) Assignees: Acclarent, Inc., Irvine, CA (US); Biosense Webster (Israel) Ltd., Yokneam (IL)

( * ) Notice: Subject to any disclaimer, the term of this patent is extended or adjusted under 35 U.S.C. 154(b) by 357 days.

(21) Appl. No.: 17/400,171

(22) Filed: Aug. 12, 2021

(65) Prior Publication Data
US 2022/0015786 A1 Jan. 20, 2022

Related U.S. Application Data

(60) Division of application No. 16/210,301, filed on Dec. 5, 2018, now Pat. No. 11,103,266, which is a
(Continued)

(51) Int. Cl.
*A61B 17/24* (2006.01)
*A61M 29/02* (2006.01)
(Continued)

(52) U.S. Cl.
CPC ............ *A61B 17/24* (2013.01); *A61B 1/0004* (2022.02); *A61B 17/320758* (2013.01);
(Continued)

(58) Field of Classification Search
CPC ............ A61B 34/20; A61B 2304/2051; A61B 1/00039; A61B 17/320758;
(Continued)

(56) References Cited

U.S. PATENT DOCUMENTS 5,373,317 A 12/1994 Salvati et al.
5,460,167 A 10/1995 Yabe et al.
(Continued)

FOREIGN PATENT DOCUMENTS

EP 1626764 A1 2/2006
EP 3020323 A1 5/2016
WO WO 2004/103449 A1 12/2004

OTHER PUBLICATIONS

Dujovny, M., et al. "Frazier Suction Cannula Fluid Control Technical Note." *Neurosurg Cases Rev* 1.005 (2018).
(Continued)

*Primary Examiner* — Jason E Flick
*Assistant Examiner* — Justin L Zamory
(74) *Attorney, Agent, or Firm* — Frost Brown Todd LLP

(57) ABSTRACT

Variations of integral navigation controls may be used in conjunction with a medical instrument to provide navigation functions for an image guided surgery (IGS) system that is in communication with the integral navigation controls. In some variations, a medical instrument with integrated navigation wheels allows movement of a cursor of the IGS system along the x and y axis by scrolling the wheel, or allows selection, zooming, or other controls by combined clicking and/or scrolling of wheels, and may be sterilized or discarded along with the device. In some other variations, a
(Continued)

control overlay may be temporarily attached to the medical instrument to provide additional controls, such as buttons or a pointing stick, and then removed and sterilized or discarded after a procedure. In each variation, inputs may be communicated via wire or wirelessly to an IGS system to provide navigation of images during a surgical procedure.

20 Claims, 19 Drawing Sheets

Related U.S. Application Data continuation-in-part of application No. 16/021,355, filed on Jun. 28, 2018.

(60) Provisional application No. 62/610,993, filed on Dec. 28, 2017.

(51) Int. Cl.
*A61B 17/3207* (2006.01)
*A61M 25/09* (2006.01)
*A61B 34/20* (2016.01)
*A61B 1/00* (2006.01)
*A61B 17/00* (2006.01)

(52) U.S. Cl.
CPC .............. *A61B 34/20* (2016.02); *A61M 25/09* (2013.01); *A61M 29/02* (2013.01); *A61B 2017/00207* (2013.01); *A61B 2017/00367* (2013.01); *A61B 2017/00424* (2013.01); *A61B 2017/00734* (2013.01); *A61B 2017/00787* (2013.01); *A61B 2017/246* (2013.01); *A61B 2034/2051* (2016.02); *A61B 2217/005* (2013.01); *A61B 2217/007* (2013.01); *A61M 2205/8206* (2013.01); *A61M 2210/0675* (2013.01); *A61M 2210/0681* (2013.01)

(58) Field of Classification Search
CPC .......... A61B 2017/00207; A61B 2017/00367; A61B 2017/00424; A61B 2017/246; A61B 2217/005; A61B 2217/007; A61M 2210/0681

See application file for complete search history.

(56) References Cited

U.S. PATENT DOCUMENTS

| | | | |
|---|---|---|---|
| 7,462,175 | B2 | 12/2008 | Chang et al. |
| 7,720,521 | B2 | 5/2010 | Chang et al. |
| 8,320,711 | B2 | 11/2012 | Altmann et al. |
| 8,702,626 | B1 | 4/2014 | Kim et al. |
| 9,155,492 | B2 | 10/2015 | Jenkins et al. |
| 11,103,266 | B2 | 8/2021 | Palushi et al. |
| 2003/0098849 | A1 | 5/2003 | Jzuhsiang |
| 2006/0044257 | A1 | 3/2006 | Chou |
| 2008/0306490 | A1 | 12/2008 | Lakin et al. |
| 2009/0221890 | A1 | 9/2009 | Saffer et al. |
| 2011/0004057 | A1 | 1/2011 | Goldfarb et al. |
| 2011/0060214 | A1 | 3/2011 | Makower |
| 2011/0251548 | A1 | 10/2011 | Thoe et al. |
| 2012/0289858 | A1 | 11/2012 | Yang et al. |
| 2013/0079665 | A1* | 3/2013 | Hibner ............... A61B 10/0275 600/567 |
| 2014/0364725 | A1 | 12/2014 | Makower |
| 2015/0182232 | A1 | 7/2015 | Peterson et al. |
| 2016/0008083 | A1 | 1/2016 | Kesten et al. |
| 2016/0310042 | A1 | 10/2016 | Kesten et al. |
| 2018/0338675 | A1* | 11/2018 | Eggli .................. A61B 1/0052 |
| 2019/0201121 | A1 | 7/2019 | Palushi et al. |
| 2019/0388117 | A1 | 12/2019 | Akbarian et al. |

OTHER PUBLICATIONS

International Search Report and Written Opinion dated May 10, 2019, for International Application No. PCT/IB2018/060374, 13 pages.

U.S. Appl. No. 62/555,824, entitled "Apparatus to Secure Field Generating Device to Chair," filed Sep. 8, 2017.

U.S. Appl. No. 62/741,594, entitled "Hollow Tube Surgical Instrument with Single Axis Sensor," filed Oct. 5, 2018.

* cited by examiner

MEDICAL INSTRUMENT WITH INTEGRAL NAVIGATION CONTROL FEATURES

PRIORITY

This application is a divisional application of U.S. non-provisional patent application Ser. No. 16/210,301, filed Dec. 5, 2018, entitled "Medical Instrument with Integral Navigation Control Features," issued as U.S. Pat. No. 11,103,266 on Aug. 31, 2021. U.S. non-provisional patent application Ser. No. 16/210,301 is a continuation-in-part of U.S. non-provisional patent application Ser. No. 16/021,355, filed Jun. 28, 2018, entitled "Medical Instrument with Integral Navigation Control Features," published as U.S. Pub. No. 2019/0201121 on Jul. 4, 2019, which itself claims the benefit of U.S. provisional patent application 62/610,993, filed Dec. 28, 2017, the disclosures of each of which are hereby incorporated by reference in their entirety.

BACKGROUND

In some instances, it may be desirable to dilate an anatomical passageway in a patient. This may include dilation of ostia of paranasal sinuses (e.g., to treat sinusitis), dilation of the larynx, dilation of the Eustachian tube, dilation of other passageways within the ear, nose, or throat, etc. One method of dilating anatomical passageways includes using a guide wire and catheter to position an inflatable balloon within the anatomical passageway, then inflating the balloon with a fluid (e.g., saline) to dilate the anatomical passageway. For instance, the expandable balloon may be positioned within an ostium at a paranasal sinus and then be inflated, to thereby dilate the ostium by remodeling the bone adjacent to the ostium, without requiring incision of the mucosa or removal of any bone. The dilated ostium may then allow for improved drainage from and ventilation of the affected paranasal sinus. A system that may be used to perform such procedures may be provided in accordance with the teachings of U.S. Pub. No. 2011/0004057, entitled "Systems and Methods for Transnasal Dilation of Passageways in the Ear, Nose or Throat," published Jan. 6, 2011, now abandoned, the disclosure of which is incorporated by reference herein. An example of such a system is the Relieva® Spin Balloon Sinuplasty™ System by Acclarent, Inc. of Irvine, California.

Image-guided surgery (IGS) is a technique where a computer is used to obtain a real-time correlation of the location of an instrument that has been inserted into a patient's body to a set of preoperatively obtained images (e.g., a CT or MRI scan, 3-D map, etc.), such that the computer system may superimpose the current location of the instrument on the preoperatively obtained images. In some IGS procedures, a digital tomographic scan (e.g., CT or MM, 3-D map, etc.) of the operative field is obtained prior to surgery. A specially programmed computer is then used to convert the digital tomographic scan data into a digital map. During surgery, special instruments having sensors (e.g., electromagnetic coils that emit electromagnetic fields and/or are responsive to externally generated electromagnetic fields) mounted thereon are used to perform the procedure while the sensors send data to the computer indicating the current position of each surgical instrument. The computer correlates the data it receives from the instrument-mounted sensors with the digital map that was created from the preoperative tomographic scan. The tomographic scan images are displayed on a video monitor along with an indicator (e.g., crosshairs or an illuminated dot, etc.) showing the real-time position of each surgical instrument relative to the anatomical structures shown in the scan images. In this manner, the surgeon is able to know the precise position of each sensor-equipped instrument by viewing the video monitor even if the surgeon is unable to directly visualize the instrument itself at its current location within the body.

An example of an electromagnetic IGS systems that may be used in ENT and sinus surgery is the CARTO® 3 System by Biosense-Webster, Inc., of Irvine, California When applied to functional endoscopic sinus surgery (FESS), balloon sinuplasty, and/or other ENT procedures, the use of IGS systems allows the surgeon to achieve more precise movement and positioning of the surgical instruments than can be achieved by viewing through an endoscope alone. As a result, IGS systems may be particularly useful during performance of FESS, balloon sinuplasty, and/or other ENT procedures where anatomical landmarks are not present or are difficult to visualize endoscopically.

Navigation of the three-dimensional views of the areas surrounding the operative field (e.g., rotating or moving a viewpoint within three-dimensional space) may be accomplished via interaction with an interface device, such as a keyboard or mouse, of an IGS system. These types of interface devices might not be intended for use in a sterile environment, and therefore may not located within reach of a clinician that is performing a medical procedure with the assistance of an IGS system. As a result, clinicians may need to relay navigation instructions to an assistant in another room or area, who will then use the interface device to provide the three-dimensional views that the clinician desires. This process can be time consuming and error prone.

While several systems and methods have been made and used in ENT procedures, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

Figure 1A:
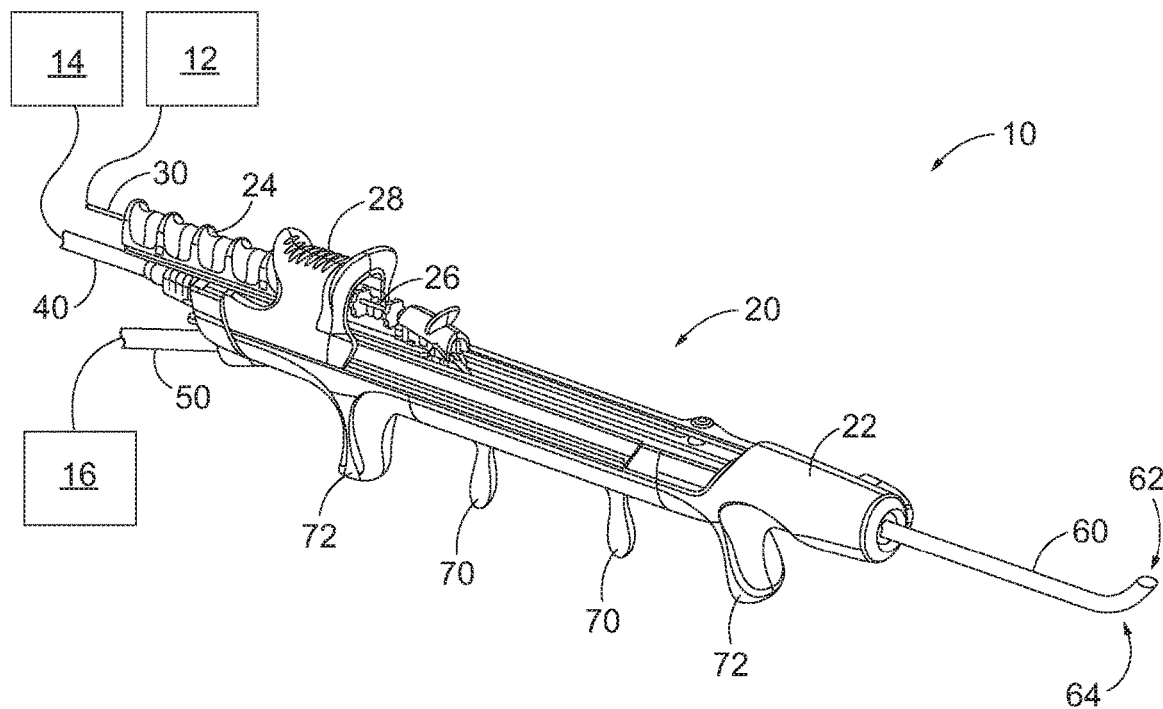
FIG. 1A depicts a perspective view of an exemplary dilation instrument assembly, with a guidewire in a proximal position, and with a dilation catheter in a proximal position.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Exemplary Dilation Catheter System

FIGS. 1A-1D show an exemplary dilation instrument assembly (10) that may be used to dilate the ostium of a paranasal sinus; to dilate some other passageway associated with drainage of a paranasal sinus; to dilate a Eustachian tube; or to dilate some other anatomical passageway (e.g., within the ear, nose, or throat, etc.). Dilation instrument assembly (10) of this example comprises a guidewire power source (12), an inflation source (14), an irrigation fluid source (16), and a dilation instrument (20). In some versions, guidewire power source (12) comprises a source of light. In some other versions, guidewire power source (12) is part of an IGS system as described below. Inflation source (14) may comprise a source of saline or any other suitable source of fluid. Irrigation fluid source (16) may comprise a source of saline or any other suitable source of fluid. Again, though, any other suitable source of fluid may be used. It should also be understood that irrigation fluid source (16) may be omitted in some versions.

Dilation instrument (20) of the present example comprise a handle body (22) with a guidewire slider (24), a guidewire spinner (26), and a dilation catheter slider (28). Handle body (22) is sized and configured to be gripped by a single hand of a human operator. Sliders (24, 28) and spinner (26) are also positioned and configured to be manipulated by the same hand that grasps handle body (22).

A guide catheter (60) extends distally from handle body (22). Guide catheter (60) includes an open distal end (62) and a bend (64) formed proximal to open distal end (62). Dilation instrument (20) is configured to removably receive several different kinds of guide catheters (60), each guide catheter (60) having a different angle formed by bend (64). Guide catheter (60) of the present example is formed of a rigid material (e.g., rigid metal and/or rigid plastic, etc.), such that guide catheter (60) maintains a consistent configuration of bend (64) during use of dilation instrument (20). In some versions, dilation instrument (20), is further configured to enable rotation of guide catheter (60) relative to handle body (22), about the longitudinal axis of the straight proximal portion of guide catheter (60), thereby further promoting access to various anatomical structures.

Figure 1B:
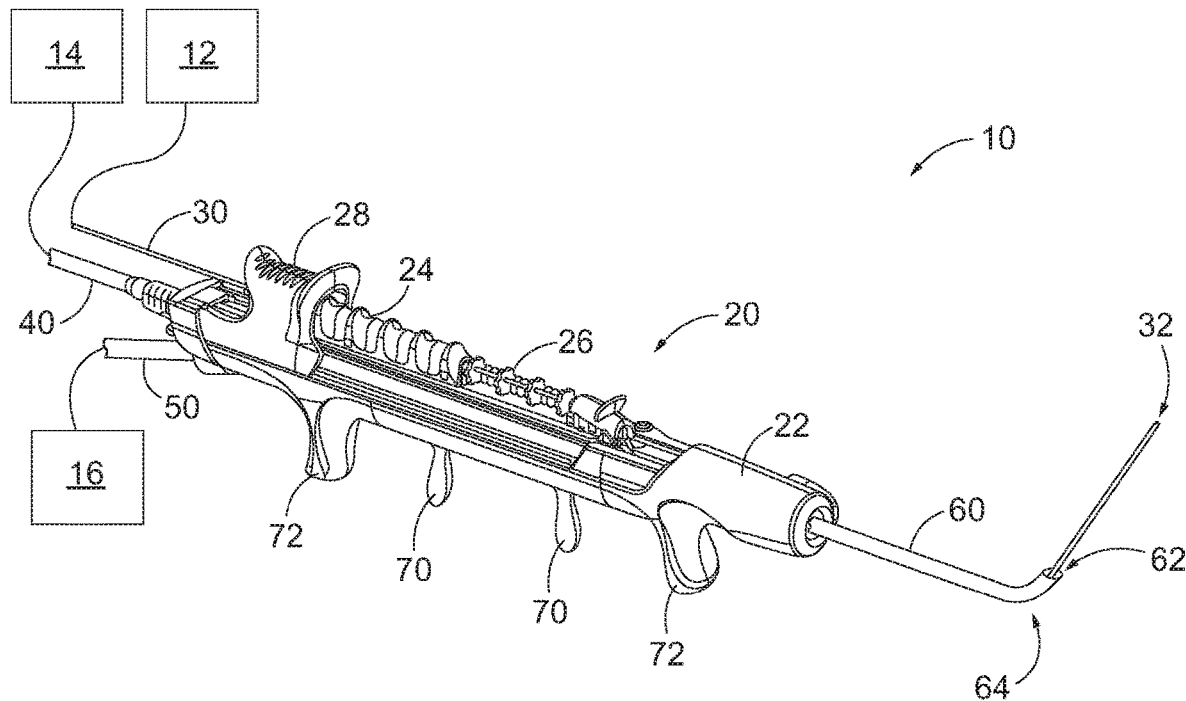
FIG. 1B depicts a perspective view of the dilation instrument assembly of FIG. 1A, with the guidewire in a distal position, and with the dilation catheter in the proximal position.

A guidewire (30) is coaxially disposed in guide catheter (60). Guidewire slider (24) is secured to guidewire (30). Translation of guidewire slider (24) relative to handle body (22) from a proximal position (FIG. 1A) to a distal position (FIG. 1B) causes corresponding translation of guidewire (30) relative to handle body (22) from a proximal position (FIG. 1A) to a distal position (FIG. 1B). When guidewire (30) is in a distal position, a distal portion of guidewire (30) protrudes distally from open distal end (62) of guide catheter (60). Guidewire spinner (26) is operable to rotate guidewire (30) about the longitudinal axis of guidewire (30). Guidewire spinner (26) is coupled with guidewire slider (24) such that guidewire spinner (26) translates longitudinally with guidewire slider (24). By way of example only, guidewire (30) may be configured in accordance with at least some of the teachings of U.S. Pat. No. 9,155,492, the disclosure of which is incorporated by reference herein. Other features and operabilities that may be incorporated into guidewire (30) will be apparent to those of ordinary skill in the art in view of the teachings herein.

Figure 1C:
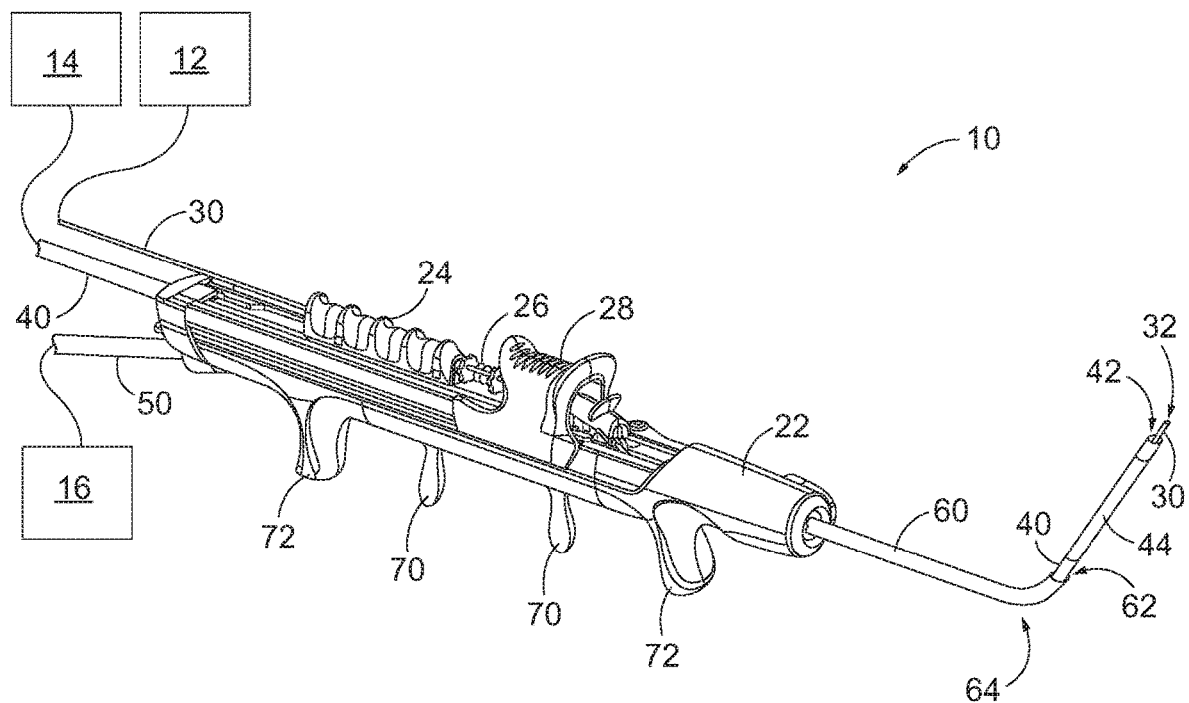
FIG. 1C depicts a perspective view of the dilation instrument assembly of FIG. 1A, with the guidewire in a distal position, with the dilation catheter in a distal position, and with a dilator of the dilation catheter in a non-dilated state.
Figure 1D:
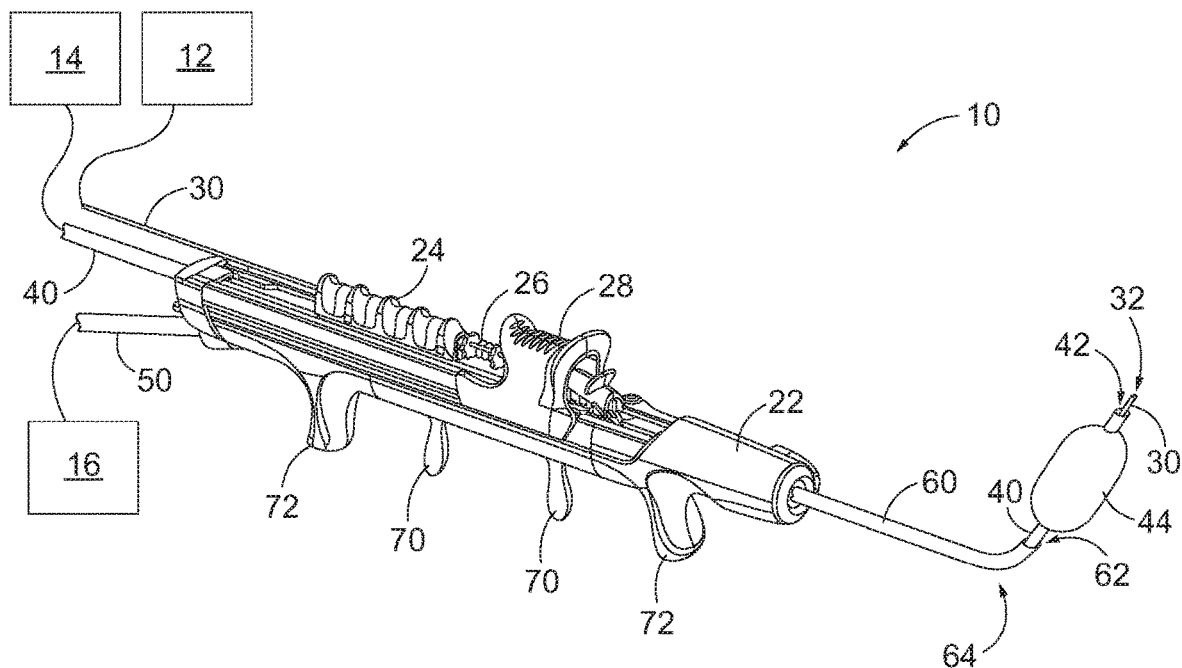
FIG. 1D depicts a perspective view of the dilation instrument assembly of FIG. 1A, with the guidewire in a distal position, with the dilation catheter in the distal position, and with a dilator of the dilation catheter in a dilated state.

A dilation catheter (40) is coaxially disposed in guide catheter (60). Dilation catheter slider (28) is secured to dilation catheter (40). Translation of dilation catheter slider (28) relative to handle body (22) from a proximal position (FIG. 1B) to a distal position (FIG. 1C) causes corresponding translation of dilation catheter (40) relative to handle body (22) from a proximal position (FIG. 1B) to a distal position (FIG. 1C). When dilation catheter (40) is in a distal position, a distal portion of dilation catheter (40) protrudes distally from open distal end (62) of guide catheter (60). Dilation catheter (40) of the present example comprises a non-extensible balloon (44) located just proximal to open distal end (42) of dilation catheter (40). Balloon (44) is in fluid communication with inflation source (14). Inflation source (14) is configured to communicate fluid (e.g., saline, etc.) to and from balloon (44) to thereby transition balloon (44) between a non-inflated state and an inflated state. FIG. 1C shows balloon (44) in a non-inflated state. FIG. 1D shows balloon (44) in an inflated state. In the non-inflated state, balloon (44) is configured to be inserted into a constricted anatomical passageway. In the inflated state, balloon (44) is configured to dilate the anatomical passageway in which balloon (44) is inserted. Other features and operabilities that may be incorporated into dilation catheter (40) will be apparent to those of ordinary skill in the art in view of the teachings herein.

II. Exemplary Image Guided Surgery Navigation System

Figure 2:
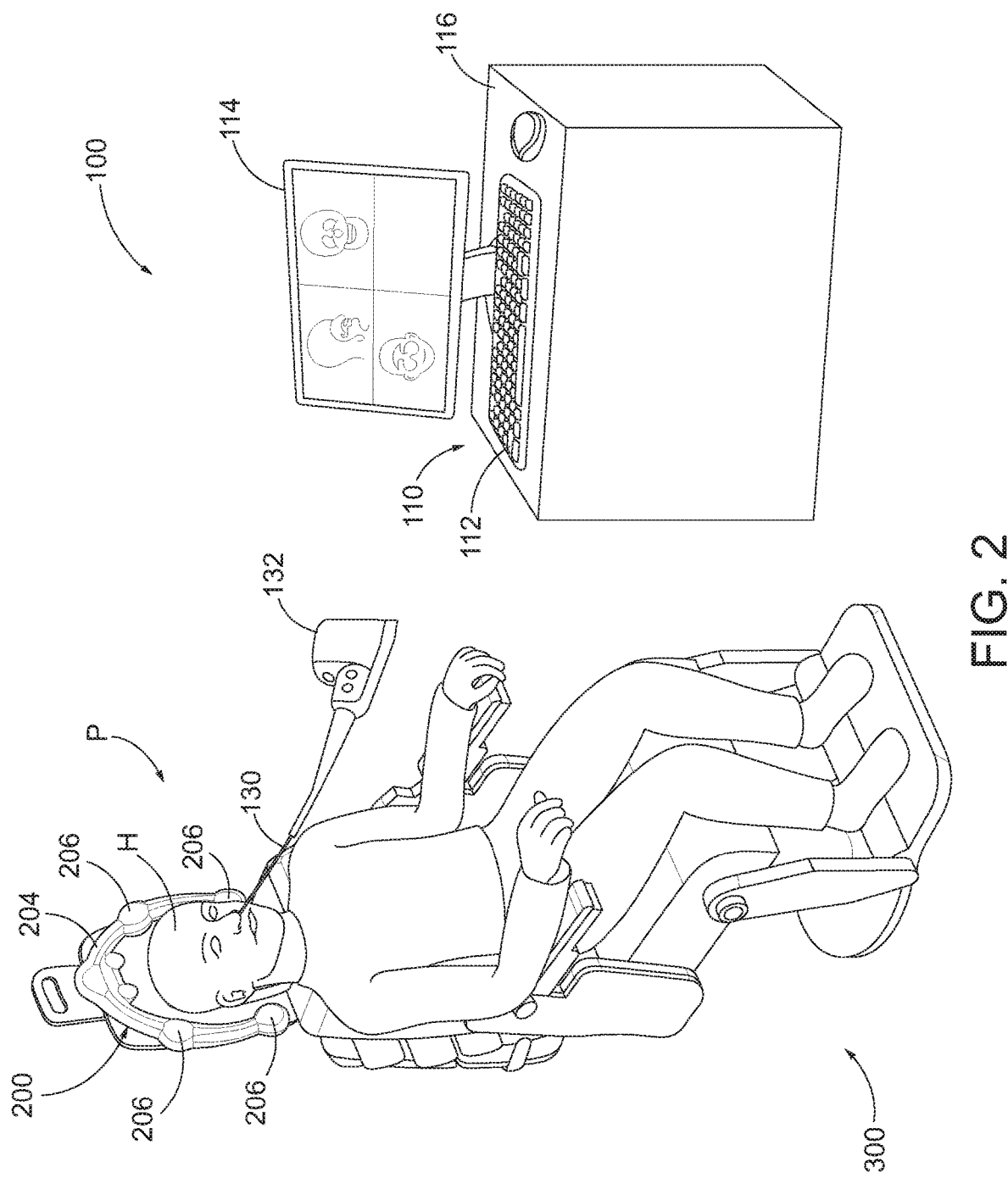
FIG. 2 depicts a schematic view of an exemplary sinus surgery navigation system being used on a patient seated in an exemplary medical procedure chair.

FIG. 2 shows an exemplary IGS navigation system (100) enabling an ENT procedure to be performed using image guidance. In some instances, IGS navigation system (100) is used during a procedure where dilation instrument assembly (10) is used to dilate the ostium of a paranasal sinus; or to dilate some other anatomical passageway (e.g., within the ear, nose, or throat, etc.). In addition to or in lieu of having the components and operability described herein IGS navigation system (100) may be constructed and operable in accordance with at least some of the teachings of U.S. Pat. No. 8,702,626, entitled "Guidewires for Performing Image Guided Procedures," issued Apr. 22, 2014, the disclosure of which is incorporated by reference herein; U.S. Pat. No. 8,320,711, entitled "Anatomical Modeling from a 3-D Image and a Surface Mapping," issued Nov. 27, 2012, the disclosure of which is incorporated by reference herein; U.S. Pat. No. 7,720,521, entitled "Methods and Devices for Performing Procedures within the Ear, Nose, Throat and Paranasal Sinuses," issued May 18, 2010, the disclosure of which is incorporated by reference herein; U.S. Pat. Pub. No. 2014/0364725, entitled "Systems and Methods for Performing Image Guided Procedures within the Ear, Nose, Throat and Paranasal Sinuses," published Dec. 11, 2014, now abandoned, the disclosure of which is incorporated by reference herein; U.S. Pub. No. 2016/0310042, entitled "System and Method to Map Structures of Nasal Cavity," published Oct. 27, 2016, issued as U.S. Pat. No. 10,362,965 on Jul. 30, 2019; and U.S. Pat. Pub. No. 2011/0060214, entitled "Systems and Methods for Performing Image Guided Procedures within the Ear, Nose, Throat and Paranasal Sinuses," published Mar. 10, 2011, now abandoned, the disclosure of which is incorporated by reference herein.

IGS navigation system (100) of the present example comprises a field generator assembly (200), which comprises set of magnetic field generators (206) that are integrated into a horseshoe-shaped frame (204). Field generators (206) are operable to generate alternating magnetic fields of different frequencies around the head of the patient. Field generators (206) thereby enable tracking of the position of a navigation guidewire (130) that is inserted into the head of the patient. Various suitable components that may be used to form and drive field generators (206) will be apparent to those of ordinary skill in the art in view of the teachings herein.

In the present example, frame (204) is mounted to a chair (300), with the patient (P) being seated in the chair (300) such that frame (204) is located adjacent to the head (H) of the patient (P). By way of example only, chair (300) and/or field generator assembly (200) may be configured and operable in accordance with at least some of the teachings of U.S. Patent App. No. 62/555,824, entitled "Apparatus to Secure Field Generating Device to Chair," filed Sep. 8, 2017, the disclosure of which is incorporated by reference herein.

IGS navigation system (100) of the present example further comprises a processor (110), which controls field generators (206) and other elements of IGS navigation system (100). For instance, processor (110) is operable to drive field generators (206) to generate electromagnetic fields; and process signals from navigation guidewire (130) to determine the location of a sensor in navigation guidewire (130) within the head (H) of the patient (P). Processor (110) comprises a processing unit communicating with one or more memories. Processor (110) of the present example is mounted in a console (116), which comprises operating controls (112) that include a keypad and/or a pointing device such as a mouse or trackball. A physician uses operating controls (112) to interact with processor (110) while performing the surgical procedure.

A coupling unit (132) is secured to the proximal end of a navigation guidewire (130). Coupling unit (132) of this example is configured to provide wireless communication of data and other signals between console (116) and navigation guidewire (130). While coupling unit (132) of the present example couples with console (116) wirelessly, some other versions may provide wired coupling between coupling unit (132) and console (116). Various other suitable features and functionality that may be incorporated into coupling unit (132) will be apparent to those of ordinary skill in the art in view of the teachings herein.

Navigation guidewire (130) may be used as a substitute for guidewire (30) in dilation instrument (20) described above. Navigation guidewire (130) includes a sensor (not shown) that is responsive to movement within the fields generated by field generators (206). In the present example, the sensor of navigation guidewire (130) comprises at least one coil at the distal end of navigation guidewire (130). When such a coil is positioned within an electromagnetic field generated by field generators (206), movement of the coil within that magnetic field may generate electrical current in the coil, and this electrical current may be communicated along the electrical conduit(s) in navigation guidewire (130) and further to processor (110) via coupling unit (132). This phenomenon may enable IGS navigation system (100) to determine the location of the distal end of navigation guidewire (130) within a three-dimensional space (i.e., within the head (H) of the patient (P)). To accomplish this, processor (110) executes an algorithm to calculate location coordinates of the distal end of navigation guidewire (130) from the position related signals of the coil(s) in navigation guidewire (130).

Processor (110) uses software stored in a memory of processor (110) to calibrate and operate system (100). Such operation includes driving field generators (206), processing data from navigation guidewire (130), processing data from operating controls (112), and driving display screen (114). Processor (110) is further operable to provide video in real time via display screen (114), showing the position of the distal end of navigation guidewire (130) in relation to a video camera image of the patient's head (H), a CT scan image of the patient's head (H), and/or a computer generated three-dimensional model of the anatomy within and adjacent to the patient's nasal cavity. Display screen (114) may display such images simultaneously and/or superimposed on each other during the surgical procedure. Such displayed images may also include graphical representations of instruments that are inserted in the patient's head (H), such as navigation guidewire (130), such that the operator may view the virtual rendering of the instrument at its actual location in real time. By way of example only, display screen (114) may provide images in accordance with at least some of the teachings of U.S. Pub. No. 2016/0008083, entitled "Guidewire Navigation for Sinuplasty," published Jan. 14, 2016, issued as U.S. Pat. No. 10,463,242 on Nov. 5, 2019, the disclosure of which is incorporated by reference herein. In the event that the operator is also using an endoscope, the endoscopic image may also be provided on display screen (114).

The images provided through display screen (114) may help guide the operator in maneuvering and otherwise manipulating instruments within the patient's head (H). When used as a substitute for guidewire (30) in dilation instrument assembly (10), navigation guidewire (130) may facilitate navigation of instrumentation of dilation instrument assembly (10) within the patient during performance of a procedure to dilate the ostium of a paranasal sinus; or to dilate some other anatomical passageway (e.g., within the ear, nose, or throat, etc.). It should also be understood that other components of dilation instrument assembly (10) may incorporate a sensor like the sensor of navigation guidewire (130), including but not limited to dilation catheter (40).

III. Exemplary Integration of Navigation Controls with Medical Instrument

Many medical instruments, such as dilation instrument (20), described above, suction instrument (602), shown in FIG. 14 and described below, and debriding instrument (1000) shown in FIG. 19 and described below, may be used in medical procedures aided by an IGS navigation system (100). These medical instruments may have various controls built into the grips or body of the device to allow end effectors, guidewires, or other device features to be activated, deployed, or otherwise manipulated during a medical procedure. Since they are located on the grips or body of the device, these controls may be quickly and easily interacted with by a clinician during a procedure, often without being required to shift their focus from a patient or move to a different position within the procedure room. Some such actuation features are positioned and configured to be manipulated by the same hand that grasps the medical instrument, such that the medical instrument is configured to enable full operation by a single hand.

Conversely, conventional IGS navigation systems (100) may require interaction with operating controls (112) such as a mouse, keyboard, or other generic interface device in order to allow navigation through the various images, views, or other data sources offered by the IGS navigation system (100). In conventional IGS navigation systems (100), such operating controls (112) may be spaced away from the clinician operating the medical instrument (e.g., dilation instrument (20), suction instrument (602), etc.); and may be in a non-sterile field. Thus, while a clinician performing a procedure may be able to view a display screen (114) or other visual output device of an IGS navigation system (100), the mouse, keyboard, or other operating control (112) may be outside of the reach of the clinician operating the medical instrument. This means that, in order for a clinician to directly navigate the views offered by an IGS navigation system (100), which may involve navigating with six degrees of freedom (e.g., moving in any of three directions within three-dimensional space, rotating in any of three within three-dimensional space), the clinician would have to leave the sterile field of the procedure room. This may be undesirable if not impossible, and, as a result, direct navigation via operating controls (112) by a clinician who is also manipulating the medical instrument may not be feasible.

Instead of having direct control over operating controls (112), clinicians who operate the medical instrument (e.g., dilation instrument (20), suction instrument (602), etc.) in the patient may relay navigation instructions to a separate person manipulating operating controls (112) of IGS navigation system (100) as navigation is needed. Even directly shifting a viewpoint within a three-dimensional set of images to locate a desired perspective can be a complex task. Having to do so by relaying voice instructions to an operator may increase the required time and risk of error associated with this already complex task.

Addressing these shortcomings may present its own difficulties. When modifying a medical instrument, many factors must be considered. Considerations may include weight, ergonomics, cost, compatibility with sterile packaging and storage, compatibility with sterilization procedures, presence of metallic components, availability of a power source, and other considerations. Discussed below are several implementations that have may provide advantageous integral controls to a medical instrument while also balancing these other considerations.

A. Image Guided Surgery Navigation with Navigation Wheel

Figure 3:
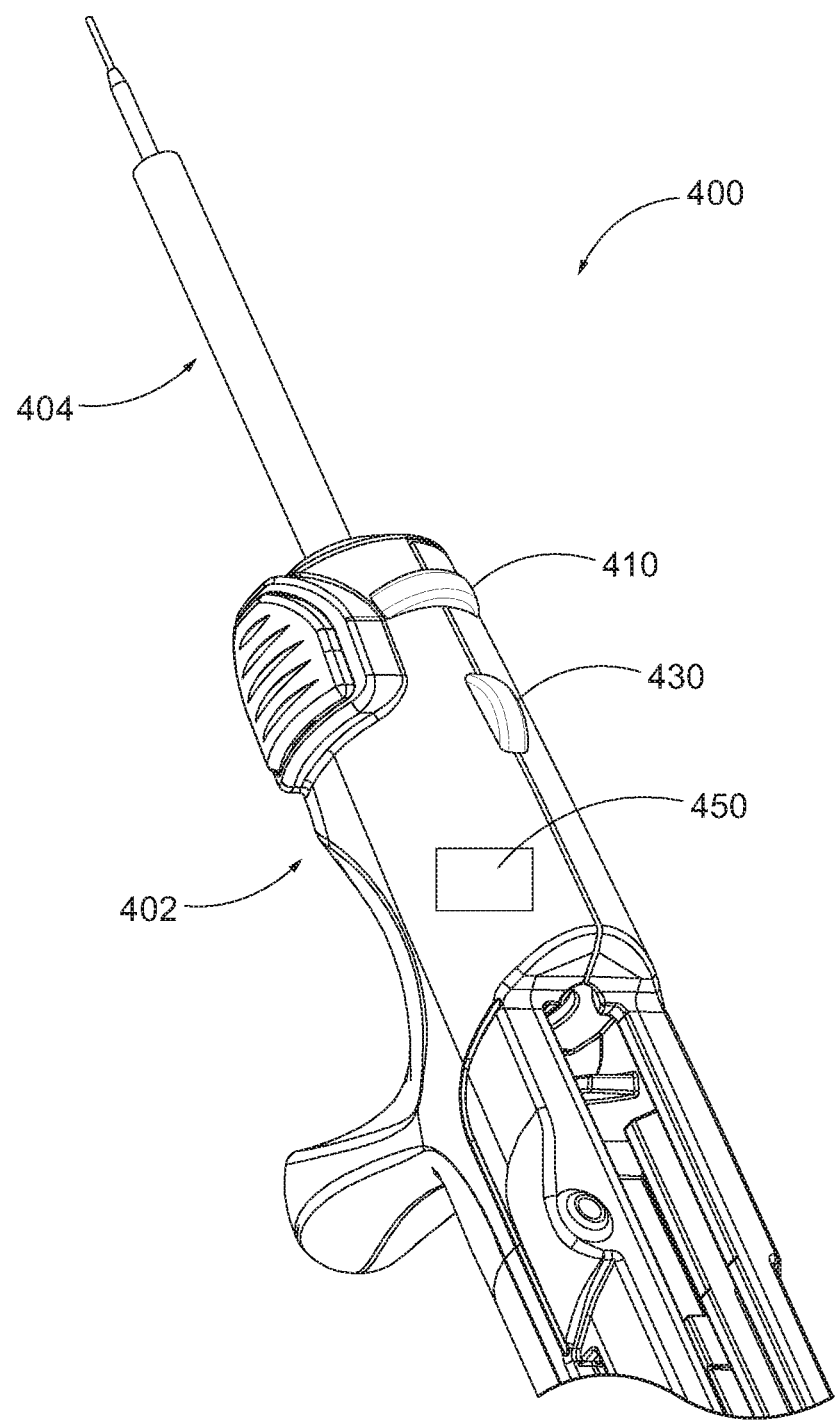
FIG. 3 depicts a perspective view of a distal portion of an exemplary dilation instrument with integral controls for IGS navigation.

FIG. 3 shows a dilation instrument (400) representing a modified version of dilation instrument (20). Thus, except as otherwise described below, dilation instrument (400) may be configured and operable just like dilation instrument (20). Dilation instrument (400) of this example includes a handle assembly (402) and a guide catheter (404) projecting distally from handle assembly (402). Dilation instrument (400)

further includes a horizontal navigation wheel (410) and a vertical navigation wheel (430) integrated into handle assembly (402).

Each navigation wheel (410, 430) is in communication with a communication module (450), which is configured to provide communication between navigation wheels (410, 430) and processor (110) of IGS navigation system (100). In some versions, communication module (450) provides wireless communication with processor (110). Such wireless communication may be provided via radio (e.g., Bluetooth, wi-fi), optical (e.g., infra-red), sonic (e.g., ultrasonic transmission), induction (e.g, RFID), or otherwise. In some other versions, communication module (450) provides wired communication with processor (110). Various suitable forms that communication module (450) may take will be apparent to those of ordinary skill in the art in view of the teachings herein.

Navigation wheels (410, 430) provide additional input options for a clinician using the dilation instrument (400), which may include scrolling or rotating the wheel in either direction, clicking or depressing the wheel downwardly like a button, tilt-clicking the wheel in either direction like a switch, and combinations of the above. These additional inputs may be communicated to an IGS navigation system (100) via communication module (450) to allow interaction with that system, and may allow a clinician using the dilation instrument (400) to change the configuration of the IGS navigation system (100), change their perspective and navigate the views offered by display screen (114), and other similar interactions.

Inputs from navigation wheels (410, 430) may be configured to provide various interactions with the IGS navigation system (100), and may be interpreted differently by an IGS software application as compared to an operating system that is configured on the IGS navigation system (100). As an example, scrolling or rotating a horizontal navigation wheel (410) in a first direction may move a mouse cursor of the IGS navigation system (100) in the first direction when an IGS software application is not currently being focused on. The same input may also move a mouse cursor when the IGS software is being focused on to allow interaction with the IGS software via a mouse cursor, or, in some implementations, may rotate a viewing perspective in three-dimensional space in the first direction.

Additionally, rotating, clicking, or tilting of the navigation wheels (410, 430) may be interpreted by the IGS navigation system (100) or its software applications as various types of mouse button inputs (e.g., right click, left click), keyboard inputs (e.g., ctrl, alt, shift, space), or custom inputs (e.g., zoom in, zoom out, minimize to desktop, open a menu, save, close, or load image sets). Combined inputs may also be interpreted differently by an IGS navigation system (100) operating system or application. For example, depressing or tilting a horizontal navigation wheel (410) while rotating a vertical navigation wheel (430) may be configured to zoom in when the vertical navigation wheel (430) is rotated in a first direction; or zoom out when vertical navigation wheel (430) is rotated in a second direction. Depressing or tilting the vertical navigation wheel (430) while the horizontal navigation wheel (410) is rotated may be configured with a different functionality, such as rotating a perspective within three-dimensional space in the first or second direction.

It will be apparent to one skilled in the art, in light of this disclosure, that combining these inputs in different ways provides a great variety of unique inputs. As an example, in one implementation having two navigation wheels (410, 430) that each may be rotated in a first direction and a second direction, and may also be clicked or depressed, there are six unique single button inputs and fifteen unique two button inputs, providing more than twenty total unique input options from just two navigation wheels (410, 430). Rotational speed of a navigation wheel (410, 430) may also be an input, with the speed of rotation scaling along with the speed of a resulting perspective rotation or zoom operation; or rotational speed thresholds may be used to determine that a slow rotation is a first unique input, a moderate rotation is a second unique input, and a fast rotation is a third unique input.

Figure 4:
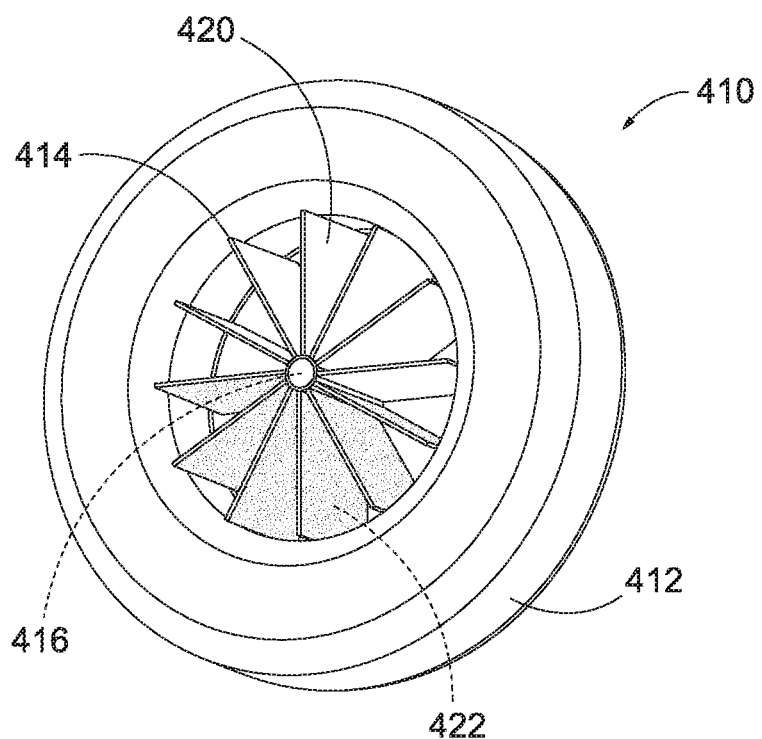
FIG. 4 depicts a perspective view of a navigation wheel used as part of the integral controls of FIG. 3.

A navigation wheel (410, 430) may be implemented in a variety of ways. FIG. 4 shows one example that may be desirable for integration with a medical instrument due to its simplicity and impact on weight and cost. The navigation wheel (410) of FIG. 4 is appropriate for use as either horizontal navigation wheel (410) or a vertical navigation wheel (430). Navigation wheel (410) of this example comprises an outer annular member (412) having a series of spokes (414) radiating from a hub (416). Each spoke (414) has a first conductive face (420) and a second conductive face (422), with each conductive face (420, 422) being connected to an electrical supply of a different voltage. For example, the first conductive face (420) may be connected to a 1-volt electrical supply, and the second conductive face (422) may be connected to a 5-volt electrical supply. The electrical supply may be delivered by a shaft (460), shown in FIG. 5, that comprises a first conductive portion (462), a second conductive portion (464) and a non-conductive portion (466).

Figure 6:
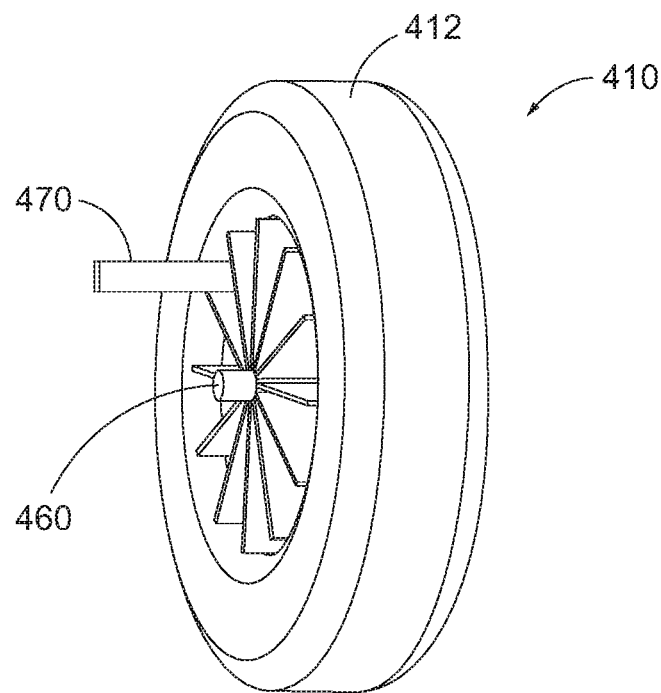
FIG. 6 depicts a perspective view of the navigation wheel of FIG. 4, the shaft of FIG. 5, and a conductive switch that form the integral controls of FIG. 3.

The shaft (460) fits within the hub (416), as shown in FIG. 6, and the first conductive portion (462) supplies a 1-volt electrical supply to the first conductive face (420) of each spoke (414). Similarly, the second conductive portion (464) supplies a 5-volt electrical supply to the second conductive face (422) of each spoke (414). The non-conductive portion (464) separates and the two conductive portions (462, 464) and, in some versions, may also have additional non-conductive materials separating the two; may be attached to the hub (416) so that the shaft (460) rotates with the annular member (412); or may rest within the hub (416) and allow the annular member (412) to rotate freely about the shaft (460).

FIG. 6 also shows a flexible conductive pin (470) that extends into the space between spokes (414). As the annular member (412) rotates, the flexible conductive pin (470) will be struck by the first conductive face (420) when the annular member (412) rotates in the first direction, and transmit, for example, a 1-volt electrical supply through the flexible conductive pin (470); or will be struck by the second conductive face (422) when the annular member (412) rotates in the second direction, and transmit, for example, a 5-volt electrical supply through the flexible conductive pin (470). Variation in the voltage supplied to the flexible conductive pin (470) may be chosen based upon factors that will be apparent to one skilled in the art. For example, in some medical instruments a 1-volt and 5-volt electrical supply may already be present in current designs for other purposes, and may be easily utilized as part of a signal generator for a navigation wheel (410, 430).

Figure 5:
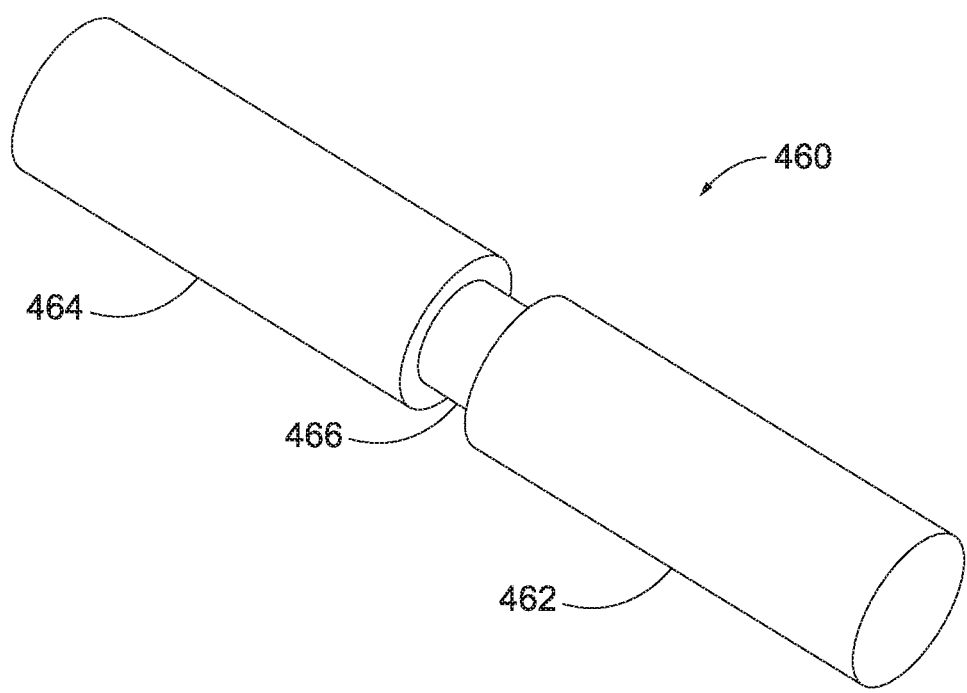
FIG. 5 depicts a perspective view of a shaft used as part of the integral controls of FIG. 3.

In operation, the navigation wheel (410) of FIGS. 4-6 will, as it is rotated by a user, generate a series of electrical signals indicating both the direction of rotation, as well as the speed of rotation. This series of signals can be interpreted by a controller (not shown) that is used by other features of dilation instrument (400), or that is dedicated for navigation wheel (410) operation. This controller may provide the signal set directly to communication module (450) that is in communication with the IGS navigation system (100), or may be perform varying levels of manipulation (e.g., filtering, encoding, interpreting, etc.) before doing so. Once received by the IGS navigation system (100), the information may be used to provide some level of control over the software of the IGS navigation system (100).

Some factors to consider in implementing a navigation wheel (410, 430) such as that shown in FIGS. 3-6 may include reusability and ease of sterilization. Some medical instruments may undergo deep sterilization treatments after each use so that they may be re-used a limited number of times. Thus, some navigation wheel (410, 430) implementations might include materials or other design choices that either prevent the need for sterilization of the wheel components (e.g., sealing the edges of the medical instrument where the wheel is installed or manufacturing components from sterile or antimicrobial materials), or improve the ability of conventional sterilization techniques to sterilize the assembly (e.g., exposing all of the non-sterile portions of the wheel assembly so that sterilant may easily enter). Various features and configurations that may be incorporated into or otherwise associated with navigation wheels (410, 430) to accommodate sterilization will be apparent to those of ordinary skill in the art in view of the teachings herein.

While the above discussion has focused on the integration of navigation wheels (410, 430) with dilation instrument (400), it should be understood that the components and features of navigation wheel (410, 430) may be integrated with a variety of medical instruments beyond dilation instrument (400), including, for example, suction instrument (602).

B. Image Guided Surgery Navigation with Control Overlay

Figure 7:
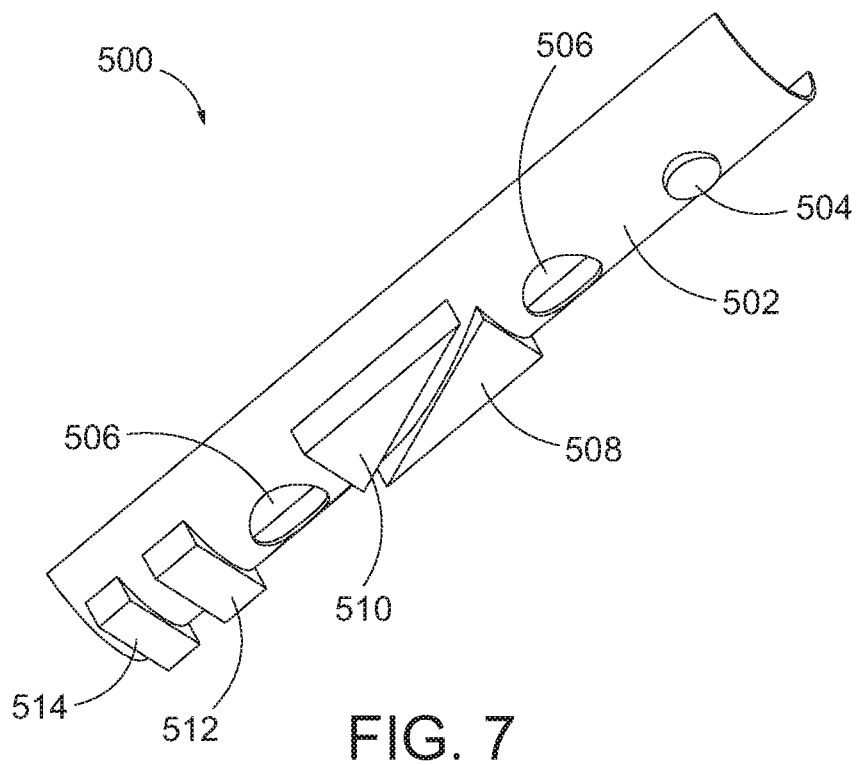
FIG. 7 depicts a perspective view of a control overlay that may be used with the dilation instrument assembly of FIG. 1A to provide integral controls for IGS navigation.
Figure 8:
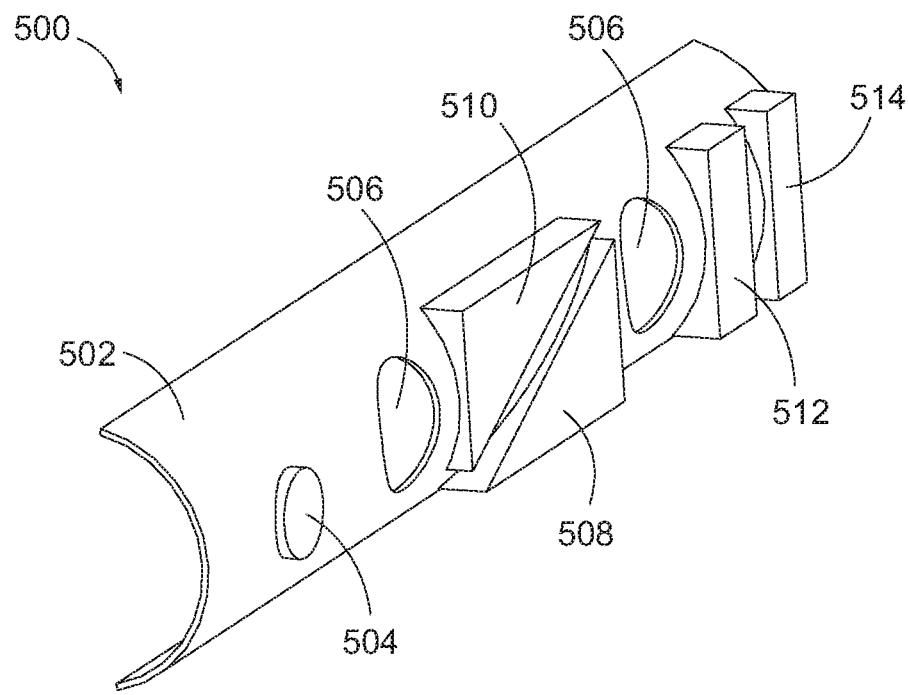
FIG. 8 depicts another perspective view of the control overlay of FIG. 7.
Figure 9:
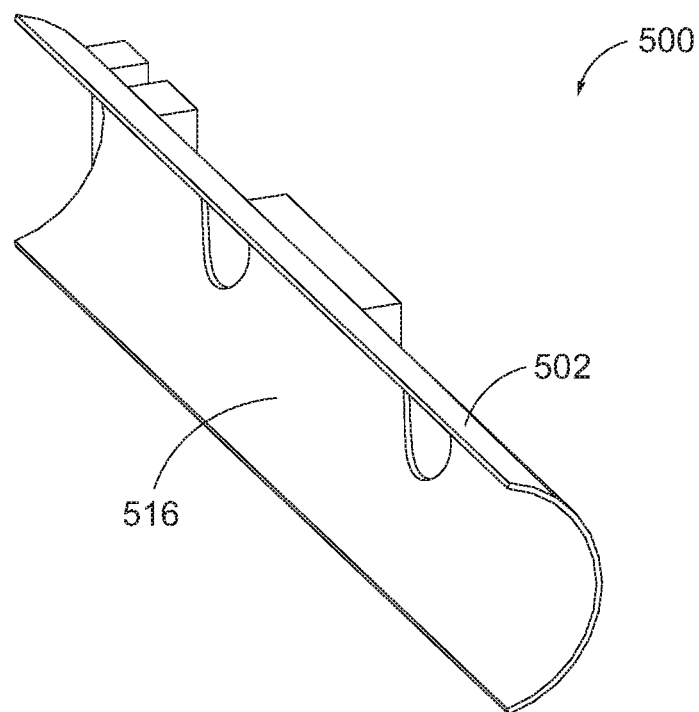
FIG. 9 depicts another perspective view of the control overlay of FIG. 7.

FIGS. 7-9 show another implementation of integral controls that may be used with a medical instrument, such as the dilation instrument (20). The control overlay (500) of FIG. 7 is designed and shaped to be placed onto the control area of the dilation instrument (20), though it may also fit other medical instruments either in the shown form, or with some changes. The control overlay (500) comprises an overlay body (502), upon which are mounted a pointing stick (504), which can be used like a joystick to provide inputs in a variety of directions (e.g., 4 directions, 8 directions, 16 directions, etc.), two midpoint buttons (508, 510), and two end buttons (512, 514), which can be pressed to provide input unique to that button. The control overlay (500) also comprises two cutouts (506) that finger-grips (70) of the dilation instrument (20) may pass through when the control overlay (500) is installed, as shown in FIG. 11.

Figure 10:
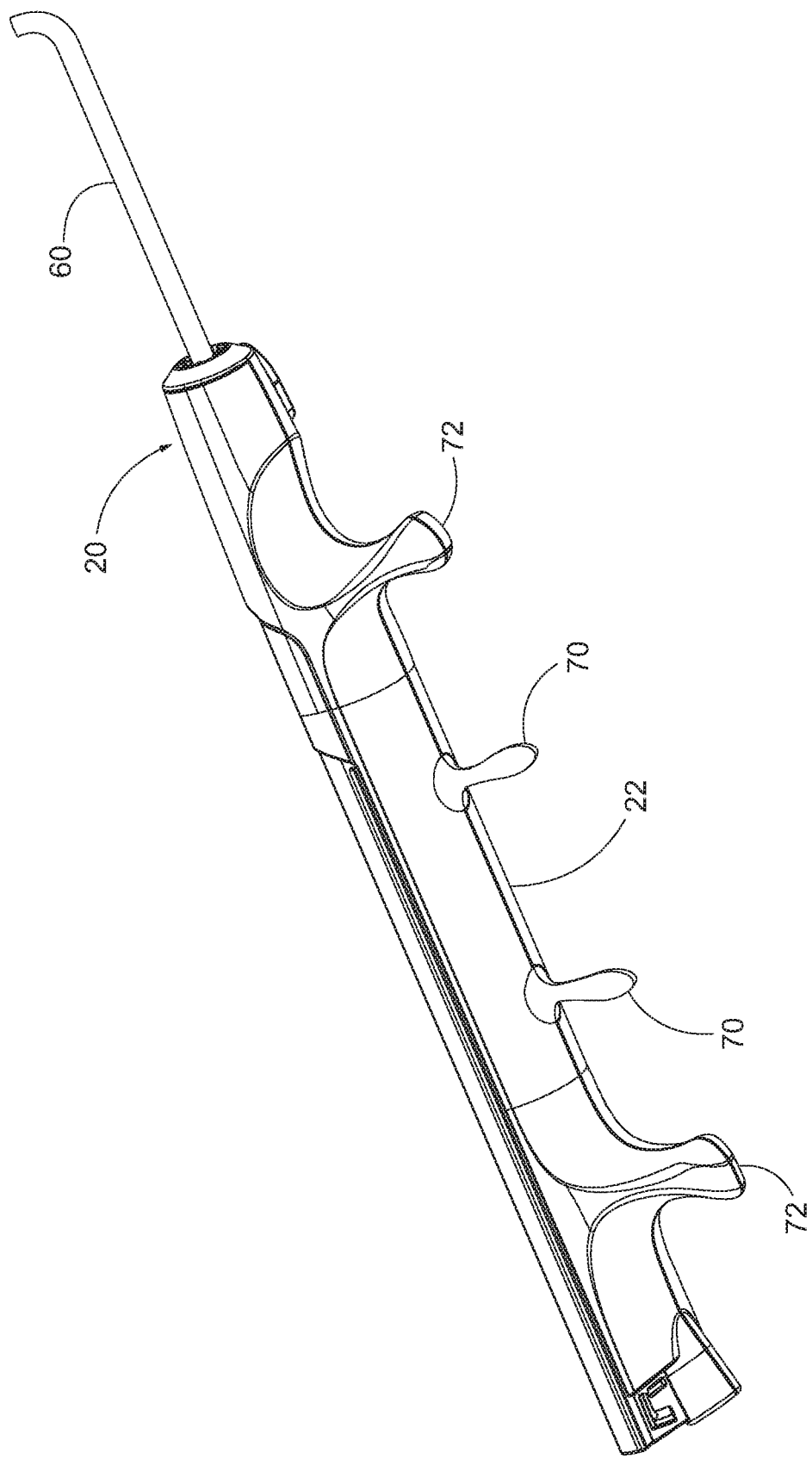
FIG. 10 depicts a perspective view of a handle body of the dilation instrument assembly of FIG. 1A.
Figure 11:
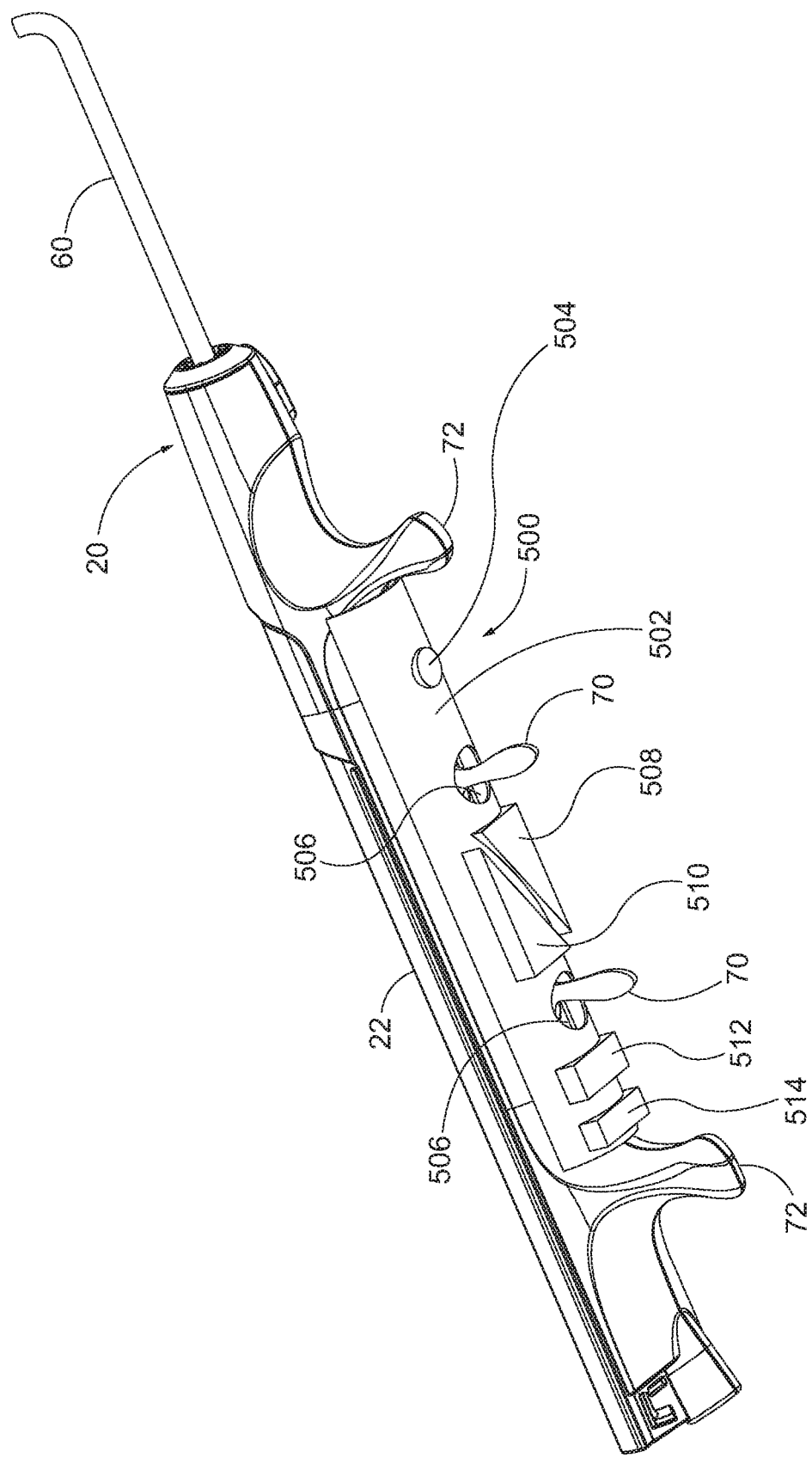
FIG. 11 depicts a perspective view of the control overlay of FIG. 7 coupled with the handle body of FIG. 10.

FIGS. 10 and 11 each show the underside of a dilation instrument assembly (10), with the control overlay (500) removed in the former, and installed in the latter. As can be seen, the control overlay (500) is of a length that allows it to fit between two outer finger-grips (72), and the cutouts (506) are positioned to allow it to slip over top of two inner finger-grips (70). The control overlay (500) is curved and contoured to substantially match the shape of the handle body (22), allowing the control overlay (500) to snugly fit against the handle body (22) when installed. This can also be seen in the rear contour (516) of the control overlay (500) in FIG. 9.

The control overlay (500) may be installed in a variety of ways. For example, in some implementations, the overlay body (502) may fit snugly between the outer finger-grips (72) such that it is held in place via friction during normal use. The edge of the overlay body (502) that contacts the outer finger-grips (72) may be constructed from or covered with an elastomeric material such as rubber or soft plastic, or have a rough, textured, or adhesive surface, in order to improve holding ability when installed in this manner. In other implementations, the control overlay (500) may be attached by way of adhesive strips or pads within the rear contour (516). In other implementations, the control overlay (500) may mechanically attach by way of clips or flexible plastic or spring-loaded catches that cause it to snap into receiver portions of the grip body (22) when pressed into position between the outer finger-grips (72). In other implementations, the control overlay (500) may be attached by way of a magnetic connection between the control overlay (500) and the grip body (22). Other ways in which the control overlay (500) could attach to the dilation instrument assembly (10) will be apparent to one skilled in the art in light of this disclosure.

As with previously discussed examples of integral controls, the pointing stick (504) and buttons (508, 510, 512, 514) of the control overlay (500) may be used singularly, or in combination with each other to provide a variety of unique inputs that can be interpreted by the IGS navigation system (100) software to provide control. As with prior examples of integral controls, inputs provided to the control overlay (500) by a user may be provided to the IGS navigation system (100) via a wireless connection (e.g., Bluetooth), or a wired connection (e.g., a USB connection present on the control overlay (500) or shared with the medical instrument).

While the control overlay (500) of FIGS. 7-9 is shaped to fit the dilation instrument assembly (10), it should be understood that the size and shape of the overlay body (502) and the position and assembly of components therein (e.g., button mechanisms, flexible Bluetooth transceiver circuit, etc.) may be varied in order to fit any medical instrument, or to provide more space within the hollow overlay body (502) for internal components (e.g., a larger battery or a haptic feedback device).

Reusability factors that may be considered in implementing an overlay control (500) might result in some implementations being produced at a cost that allows them to be disposable, removing the need for sterilization, or by providing an overlay body (502) that is entirely sealed to prevent the entry of bacteria or sterilant.

While the above discussion has focused on the control overlay (500) with dilation instrument (10), it should be understood that the components and features of control overlay (500) may be implemented and used with a variety of medical instruments beyond dilation instrument (10), including, for example, suction instrument (602).

C. Image Guided Surgery Navigation with Control Clip

Figure 12A:
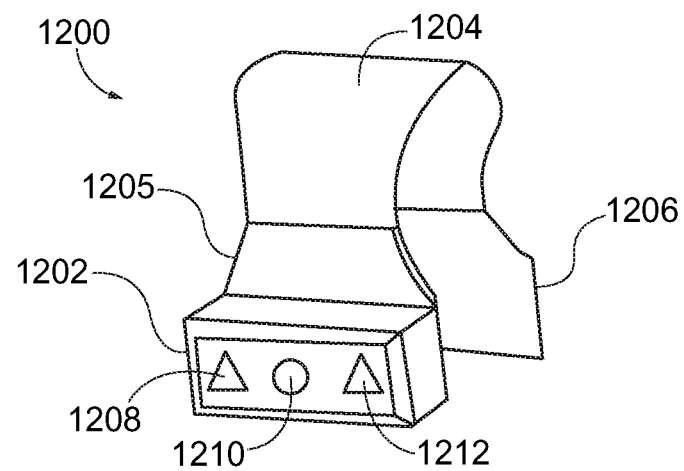
FIG. 12A depicts a perspective view of an exemplary control clip usable with a surgical instrument such as that shown in FIGS. 1A-1D.
Figure 12B:
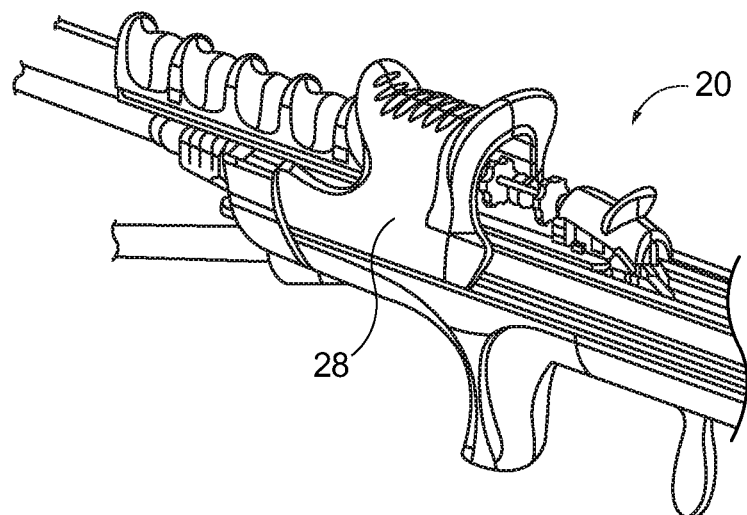
FIG. 12B depicts a perspective view of a surgical instrument dilation catheter slider which may receive the control clip of FIG. 12A.
Figure 13:
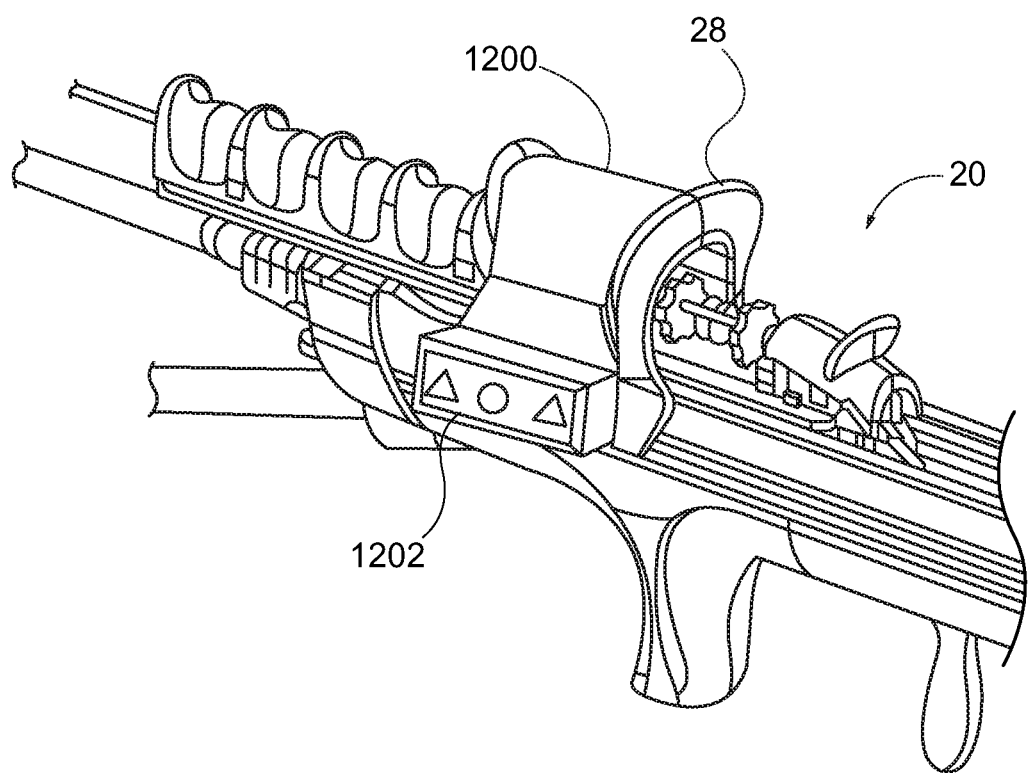
FIG. 13 depicts a perspective view of the control clip of FIG. 12A secured to the dilation catheter slider of FIG. 12B.

FIGS. 12A, 12B, and 13 show an implementation of an exemplary control clip (1200) that may be used as a retrofit with a surgical instrument, such as dilation instrument (20), to provide additional controls that may be configured to interact with a system such as the IGS navigation system (100). The control clip (1200) may be contoured and shaped to fit on a portion of a surgical instrument, such as the dilation catheter slider (28) of the dilation instrument (20), as can be seen in FIG. 13. Placement of the control clip (1200) on the dilation catheter slider (28) may advantageously position the control clip (1200), and a control module (1202) including a set of buttons or other controls, so that it is readily accessible by a user of the dilation instrument (20) to interact with the IGS navigation system (100) in order to change or interact with a software or interface shown on the display screen (114), change the operation or configuration of a surgical instrument, or other interactions.

The control clip (1200) of this example includes a first clamp arm (1205) and a second clamp arm (1206) connected by a device saddle (1204). The device saddle (1204) may be sized and contoured to fit over the grip portion of the dilation catheter slider (28), with the first clamp arm (1205) and the second clamp arm (1206) fitting on either side. In some implementations, the control clip (1200) may be constructed from resilient materials such as plastic that allow it to be fit over the dilation catheter slider (28) such that the first clamp arm (1205) and the second clamp arm (1206) are pushed outwardly, while being flexibly biased toward their original state, resulting in a friction fit or snap fit of the control clip (1200) on the dilation catheter slider (28). In some implementations, the interior side of the control clip (1200) that contacts the dilation catheter slider (28) may include adhesives, high friction flexible foams or other elastomeric material, mechanical catches that align and attach to corresponding features of the dilation catheter slider (28), or other clips, fasteners, or connectors that aid in maintaining a connection of the control clip (1200) to the dilation catheter slider (28). The control clip (1200) may also include other attachment features such as described above in the context of the control overlay (500), including textured surfaces, spring loaded catches, clips, and magnetic connections. Varying implementations may include one or more of the above attachment features, such as a control clip (1200) that is rigid but that includes an adhesive on the interior portion so that it can be temporarily adhered to the dilation catheter slider (28), or such as a control clip (1200) that is flexibly biased and includes high friction rubbers on the interior portion to aid in achieving a high friction connection to the dilation catheter slider (28).

Figure 15:
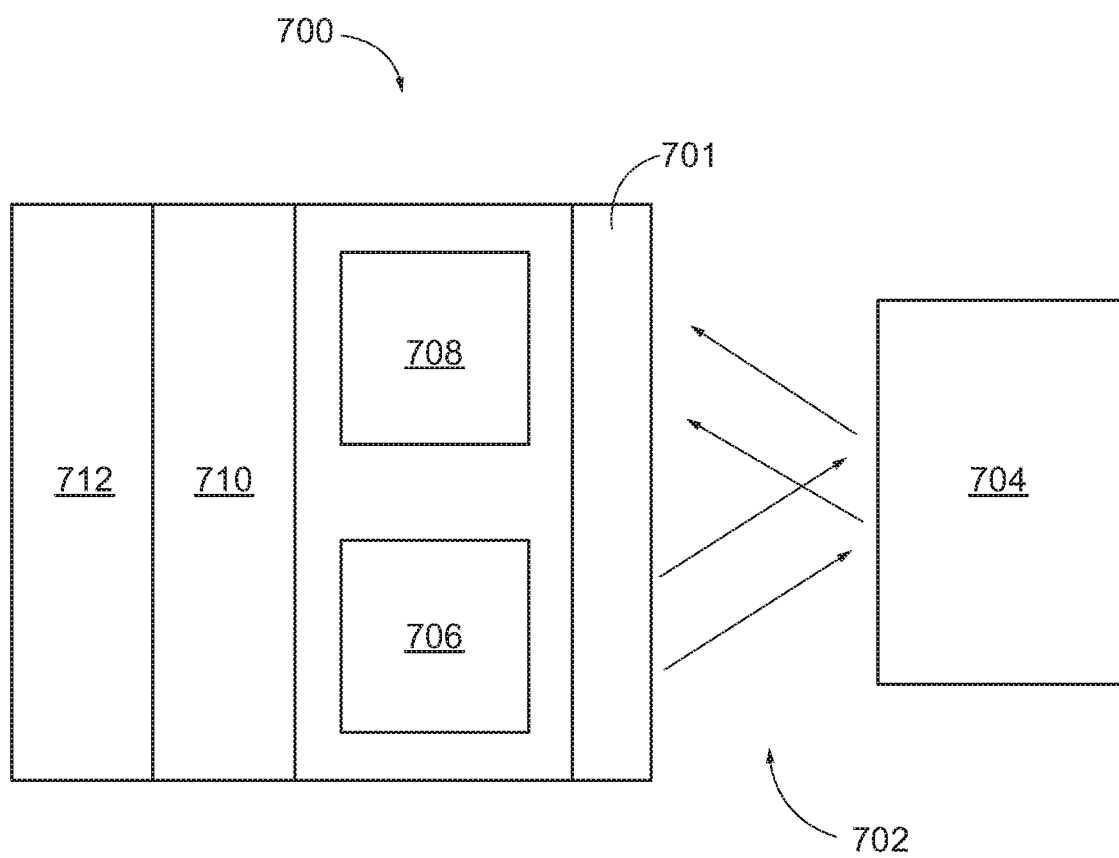
FIG. 15 depicts a schematic diagram of an exemplary proximity sensor.

The control clip (1200) of the present example also includes a control module (1202), which itself includes a first button (1208), a second button (1210), and a third button (1212). While the control module (1202) of FIG. 12A includes three buttons, it should be understood that varying implementations may include other numbers and types of controls, including, for example, navigational wheels (e.g., such as the navigation wheels (410, 430)), proximity or touch controls (e.g., such as shown in FIG. 15 and described below), sand other input types. As with previously discussed examples, the first button (1208, second button (1210), and third button (1212) may be used singularly, or in combination with each other to provide a variety of unique inputs that can be interpreted by the IGS navigation system (100) to allow control and interaction with the navigation software or other software or instruments. Inputs provided via interactions with the buttons or other controls of the control module (1202) may be provided to the IGS navigation system (100) via a wireless connection (e.g., Bluetooth, Wi-Fi, optical transmission), or a wired connection (e.g., a USB connection or other data connections present on the control overlay (500) or shared with the medical instrument).

While the control clip (1200) is shaped to fit the dilation catheter slider (28), it should be understood that the size and shape of the control clip (1200) may be varied to fit other medical instruments, to increase the size of the control module (1202) to provide more exterior surface for input controls, or additional space for internal components supporting such exterior controls. The control clip (1200) may also be implemented such that it may be disposed of after one or several uses, with such implementations including one or more low cost components such as simple actuation buttons, short range wireless communication components, low capacity batteries, and simple attachment features such as adhesives or elastomeric rubber. Some implementations may be designed for reusability; and may include one or more features such as the control module (1202) being sealed to prevent contamination during use or damage during sterilization procedures, a rechargeable battery, a rigid body that will not change shape or lose flexibility from exposure to heat, and attachments features such as mechanical catches, clips, or spring loaded switches.

D. Image Guided Surgery Navigation with Touch Sensors

Figure 14:
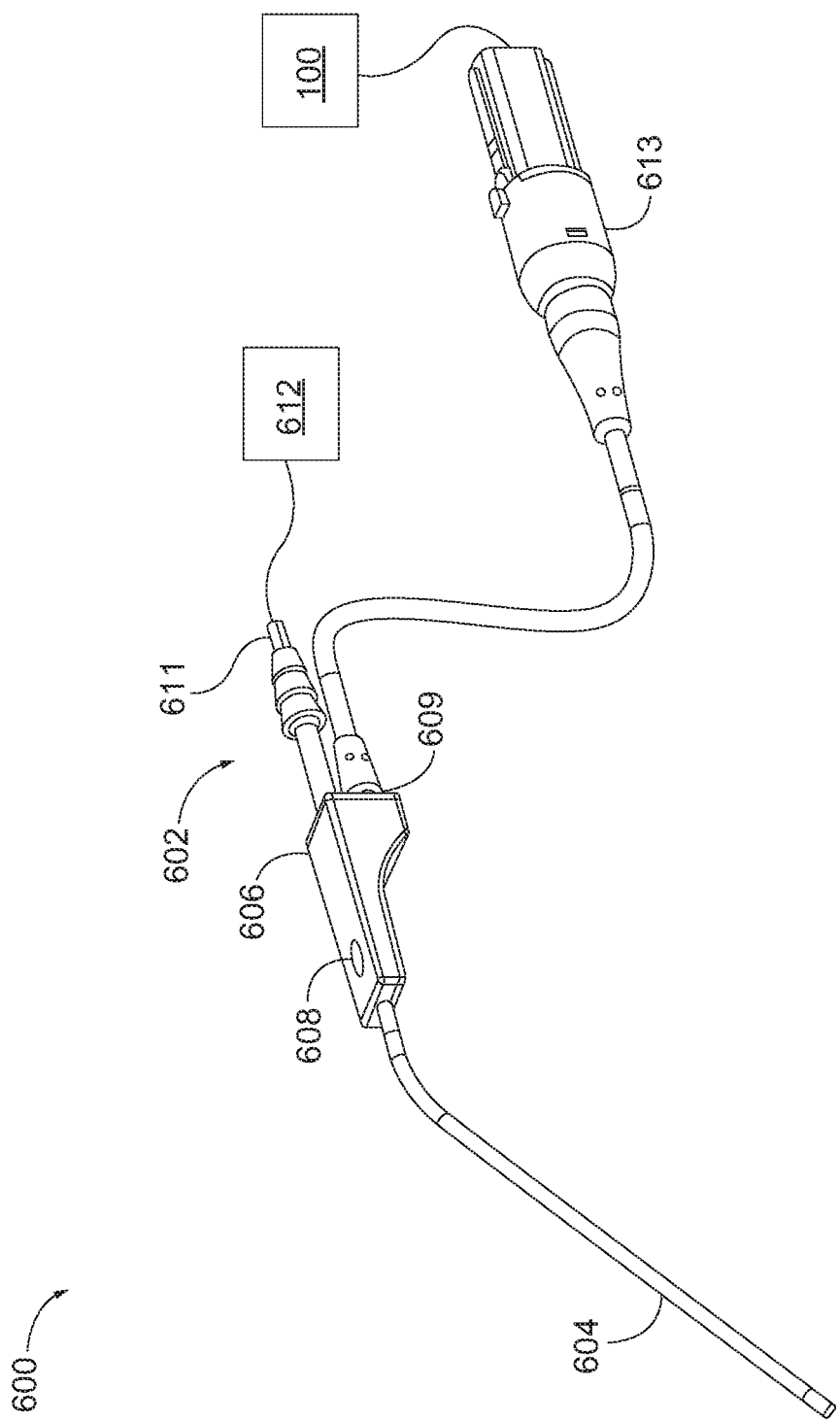
FIG. 14 depicts a perspective view of an exemplary suction instrument assembly.

FIG. 14 shows a suction instrument assembly (600) comprising a suction instrument (602) and suction source (612). Suction source (612) is connected to a suction port (611) of suction instrument (602) such that suction provided by suction source (612) is capable of producing suction through a suction cannula (604) of the suction instrument (602). In this manner, suction instrument (602) may be used during a medical procedure to remove various fluids or other materials from a procedure area and transport them, via the suction path (not pictured) of the suction instrument (602), the suction path (not pictured) comprising a channel that runs from suction cannula (604), through grip portion (606) through suction port (611) and to a disposal destination downstream of the suction port (611). Suction instrument (602) further comprises a grip portion (606) adapted to be held by a user of the suction instrument (602) during use, the grip portion (606) itself comprising a control vent (608). Control vent (608) is connected to suction path (not pictured) defined in grip portion (606) between suction cannula (604) and suction port (611) such that suction provided by suction source (612) may produce variable amounts of suction through control vent (608) and suction cannula (604) depending upon full coverage, partial coverage, or non-coverage of control vent (608) by a finger, thumb, or other surface of a user.

Suction instrument (602) is in communication with IGS navigation system (100) via a connector (613) that attaches to a port (609) of the suction instrument (602) to allow communication between the suction instrument (602) and the IGS navigation system (100). In some implementations, suction instrument (602) may also receive electrical power via the port (609) and the connector (613). Suction instrument (602) is configured to provide information to the IGS navigation system (100) that can be used to execute an algorithm to calculate location coordinates of one or more portions of suction instrument (602). For instance, a sensor like the sensor of navigation guidewire (130) may be positioned at the distal end of suction cannula (604). IGS navigation system (100) may process signals from the sensor of suction instrument (102) such that IGS navigation system (100) may calculate, track, and display the spatial location of suction cannula (604) relative to a three-dimensional model of the anatomy within or adjacent to a patient's nasal cavity.

As with other uses of the IGS navigation system (100), it may be advantageous to provide controls for the IGS navigation system (100) that are integrated with or otherwise located proximately to the suction instrument (602). Due to the relatively small size of suction instrument (602) and grip portion (606) in particular, as well as the placement and function of control vent (608), it may be advantageous to provide such controls for IGS navigation system (100) having a reduced size such that internal space and external space required for integrating the controls are minimized. Such controls could be more flexibly integrated with surgical instruments such as suction instrument (602) while not interfering with the primary function and features of the instrument, such as control vent (608) and suction path (not pictured).

FIG. 15 shows a schematic diagram of an exemplary proximity sensor (700). The proximity sensor (700) comprises an optical transmitter (706) that is operable to project a light (702) at a target (704) and an optical receiver (708) that is operable to receive the light (702) as it reflects off the target (704). The light (702) may be transmitted and received through a cover (701) of the proximity sensor (700) that is configured to allow the light (702) to pass while also providing protection to internal components of the proximity sensor (700). A controller (710) of the proximity sensor (700) is configured to control the optical transmitter (706) and receive data from the optical receiver (708) indicating characteristics of the light (702) as it is received. Characteristics may include, for example, intensity of the reflected light, angle of the reflected light, a received portion of reflected light (e.g., where the target (704) is positioned to reflect some but not all of the light projected by the optical transmitter (706)), or time between transmission and receipt. Such data may then be used by the controller (710) or be provided to another device via an input output interface (712), to calculate and determine the distance between the proximity sensor (700) and the target (704).

While proximity sensor (700) is in the form of an optical sensor in the present example, proximity sensor (700) may alternatively take various other forms. By way of example only, proximity sensor may comprise a capacitive sensor and/or any other suitable kind of proximity sensor. Other suitable examples will be apparent to those skilled in the art in view of the teachings herein.

The input output interface (712) may be a physical or wireless connection with another device or component, and may include, for example, a conductive connection capable of transmitting electrical signals, or a wireless transceiver capable of wireless communication with other devices. In some implementations, the proximity sensor (700) may be provided power via the input output interface (712), or may use an integral battery, or both. Operating in this manner, the proximity sensor (700) may provide a signal to another device or component via the input output interface (712) that indicates a verified presence of the target (704) within a detectable distance, the distance between the target (704) and the proximity sensor (700), or both.

In the context of integrated controls having a minimized size requirement, the proximity sensor (700) may be used to generate signals indicating the presence of a user's finger or other object that is touching or proximate to the proximity sensor (700); and communicate those signals via the input output interface (712) to a surgical instrument, IGS navigation system (100), or both. Such an indication could be interpreted as a user interaction with the integrated control, similarly to the pressing of a button, scrolling of a wheel, or other similar interfaces. The proximity sensor (700) may offer several advantages in such an implementation. For example, due to its relative lack of complexity and low power requirement, the proximity sensor (700) may be implemented having a small size requirement and trivial weight; and can be integrated with a surgical instrument such as the suction instrument (602) without significantly impacting its overall weight or power requirements, and without significantly impacting usability factors such as the size or shape of the grip portion (606), or the size or placement of the control vent (608).

The proximity sensor (700) may also be an advantageous control for surgical instruments such as the suction instrument (602) since it relies upon the transmission of light, which may pass through the cover (701) without impacting the performance of the proximity sensor (700). Thus, the cover (701) may seal and protect the internal portions of the proximity sensor (700) against outside liquids, gasses, or contaminants without preventing its function. In the context of surgical instruments, this may be advantageous to preserve sterility of a surgical instrument by preventing contaminants from undesirably entering or being deposited in a crack, seam, or other internal cavity of the surgical instrument before or during a procedure. This may also advantageously protect the components of the proximity sensor (700) during sterilization or reprocessing treatments of the surgical instrument before or after a procedure, which may cause sterilant, detergent, or other substances to be applied to the surgical instrument at varying pressures and temperature, which could otherwise damage or otherwise negatively impact the controller (710), optical transmitter (706), optical receiver (708), input output interface (712), or other components of the proximity sensor (700).

Figure 16:
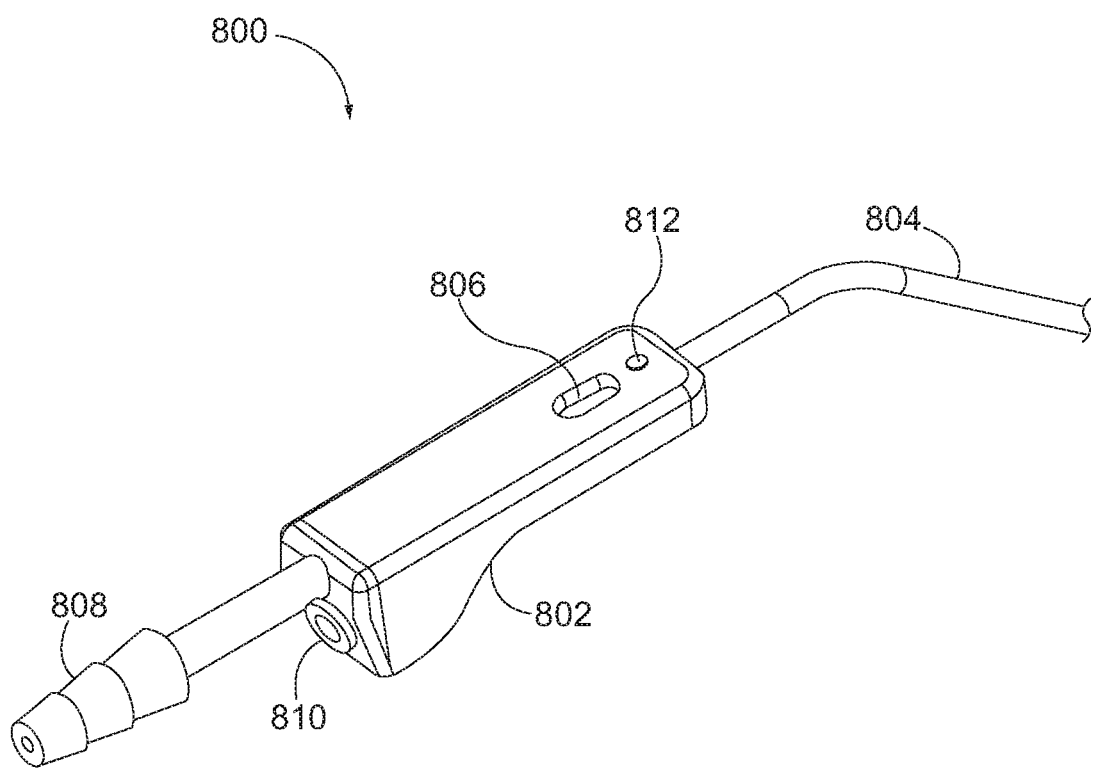
FIG. 16 depicts a perspective view of a proximal portion of an exemplary suction instrument with an integrated proximity sensor.

As an example of a surgical instrument with an integrated control similar to the proximity sensor (700) of FIG. 15, FIG. 16 shows an exemplary suction instrument (800) with a proximity control (812). The suction instrument (800) has a similar function and design as the suction instrument (602), and comprises a grip portion (802), a suction cannula (804), a control vent (806), a suction port (808), and a navigation port (810), each having a similar function as the corresponding components of the suction instrument (602). The proximity control (812) is positioned proximate to the control vent (806), to allow a user of the suction instrument (800) to swiftly alternate between covering some or all of the control vent (806) with a finger, to interacting with the proximity control (812) with the same or a different finger. The small size of the proximity control (812), both on the exterior and interior of the suction instrument (800), allows it to be integrated with the grip portion (802) without impacting the usability of the control vent (806), and without obstructing the flow of suctioned materials passing through the grip portion (802).

While FIG. 16 shows the proximity control (812) positioned on the top of the grip portion (802), proximity control (812) may also be positioned on a side or bottom of the grip portion (802), as may be desired. Similarly, while proximity control (812) is distal to control vent (806) in this example, proximity control (812) may instead be proximal to control vent (806).

The proximity control (812) may be coupled with the port (810) via circuitry embedded in the grip portion (802) such that it receives power and exchanges data with a device such as the IGS navigation system (100) that may be connected to the port (810) during use. In this manner, signals generated by a user's interactions with the proximity control (812) may be communicated to the IGS navigation system (100) as user inputs. These user inputs allow interaction with IGS navigation system (100), and may allow a clinician using the suction instrument (800) to change the configuration of the IGS navigation system (100), change their perspective and navigate the views offered by display screen (114), and other similar interactions. As with prior examples, these inputs may also be configured to provide various interactions with the IGS navigation system (100) depending upon factors such as the number, pattern, timing, and other characteristics of the inputs.

As an example, tapping the proximity control (812) once might cause the IGS navigation system (100) to proceed to a next view or image in a set of images, while double tapping the proximity control (812) might cause the IGS navigation system (100) to return to a prior view or image. An input from tapping the proximity control (812) and maintaining the tap for a period of time may cause the IGS navigation system (100) to rapidly iterate through a set of views or images, or alternatingly zoom in and zoom out from a current view. A single tap followed by moving a finger to variable distances from the proximity control (812) may cause the IGS navigation system (100) to zoom to various levels of magnification of an image dependent upon the distance of the finger from the proximity control (812). With implementations where the proximity control (812) can detect partial coverage by an object (e.g., a finger tap or touch covering only half of the proximity control (812)), user inputs could also include swiping across the proximity control (812) in different directions to control a mouse pointer, rotate a view or image, or scroll along a view or image. Other possible inputs and variations of inputs exist for the suction device (800) and IGS navigation system (100) and will be apparent to one skilled in the art in light of this disclosure.

Figure 17:
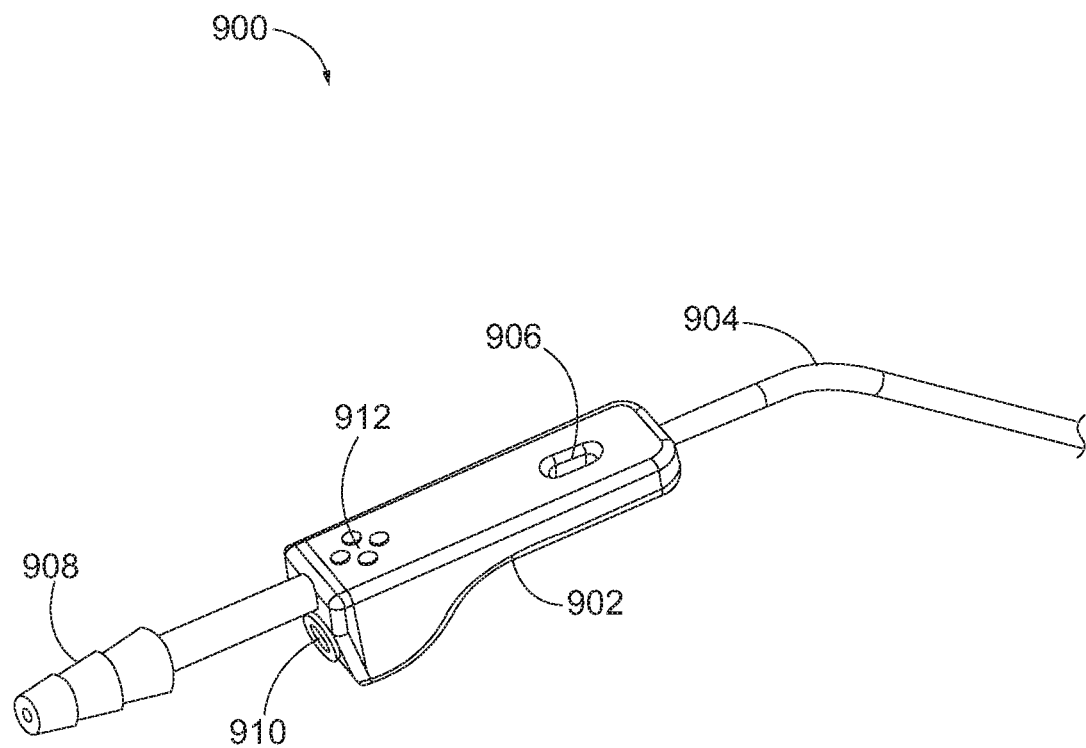
FIG. 17 depicts a perspective view of a proximal portion of another exemplary suction instrument with a set of integrated proximity sensors.

FIG. 17 shows another exemplary suction instrument (900) with an integrated control comprising a set of proximity sensors (912) similar to the proximity sensor (700). The suction instrument (900) has a similar function and design as the suction instrument (602) and suction instrument (800), and comprises a grip portion (902), an exemplary medical procedure feature shown as a suction cannula (904), a control vent (906), a suction port (908), and a navigation port (910), each having a similar function as the corresponding components of suction instrument (602, 800). An exemplary set of controls shown as a proximity control cluster (912) is positioned on the grip portion (902), to allow a user of the suction instrument (900) to swiftly alternate between covering some or all of the control vent (906) with a finger, to interacting with the proximity control cluster (912) with the same or a different finger. As with the suction instrument (800), the small size of the proximity control cluster (912), both on the exterior and interior of the suction instrument (900), allows it to be integrated with the grip portion (902) without impacting the usability of the control vent (906), and without obstructing the flow of suctioned materials passing through the grip portion (902).

While FIG. 17 shows the proximity control cluster (912) positioned on the top of the grip portion (902), proximity control cluster (912) may also be positioned on a side or bottom of the grip portion (902), as may be desired. Similarly, while proximity control cluster (912) is proximal distal to control vent (906) in this example, proximity control cluster (912) may instead be distal proximal to control vent (906).

As with the suction instrument (800), the proximity control cluster (912) may be coupled with the port (910) via circuitry embedded in the grip portion (902) such that it receives power and exchanges data with a device such as the IGS navigation system (100) that may be connected to the port (910) during use. In this manner, signals generated by a user's interactions with the proximity control cluster (912) may be communicated to the IGS navigation system (100) as user inputs. These user inputs allow interaction with that system and may allow a clinician using the suction instrument (900) to change the configuration of the IGS navigation system (100), change their perspective and navigate the views offered by display screen (114), and other similar interactions. As with prior examples associated with the suction instrument (800), these inputs may also be configured to provide various interactions with the IGS navigation system (100) depending upon factors such as the number, pattern, timing, and other characteristics of the inputs.

As an example, since the proximity control cluster (912) pictured in FIG. 17 has four separate proximity sensors similar to the proximity sensor (700), arranged in a diamond pattern with each sensor being associated with a direction (e.g., left, right, up, down), a touch or tap on an individual proximity sensor of the proximity control cluster (912) could cause the IGS navigation system to move a mouse cursor in that direction, or to navigate, scroll, or zoom images or views. Patterns of taps could also cause certain resulting actions by the IGS navigation system (100). For example, sensor tapping pattern of left, right, left, right might cause the IGS navigation system (100) to return to a pre-set view or perspective, while a pattern of up, down, up, down, may cause the IGS navigation system (100) to save a current view or perspective as the pre-set view or perspective. The proximity control cluster (912) may also support a scrolling motion across the cluster (912) to cause the view or perspective to scroll, rotate, or zoom, or a clockwise or counter-clockwise rotational motion around the perimeter of the proximity control cluster (912) to cause the view or perspective to rotate or zoom. The proximity control cluster (912) could also receive as input various motions or movements of an object within a detectable distance above the proximity control cluster (912) so that, for example, a tap of the entire proximity control cluster (912) followed by the movement of that finger in three dimensional space above the proximity control cluster (912) could be used by the IGS navigation system (100) to similarly move a viewing perspective through the three dimensional space of a navigational image set. Other possible inputs and variations of inputs exist for the suction device (900) and IGS navigation system (100) and will be apparent to one skilled in the art in light of this disclosure.

E. Image Guided Surgery Navigation with Integrated Controls

Figure 18:
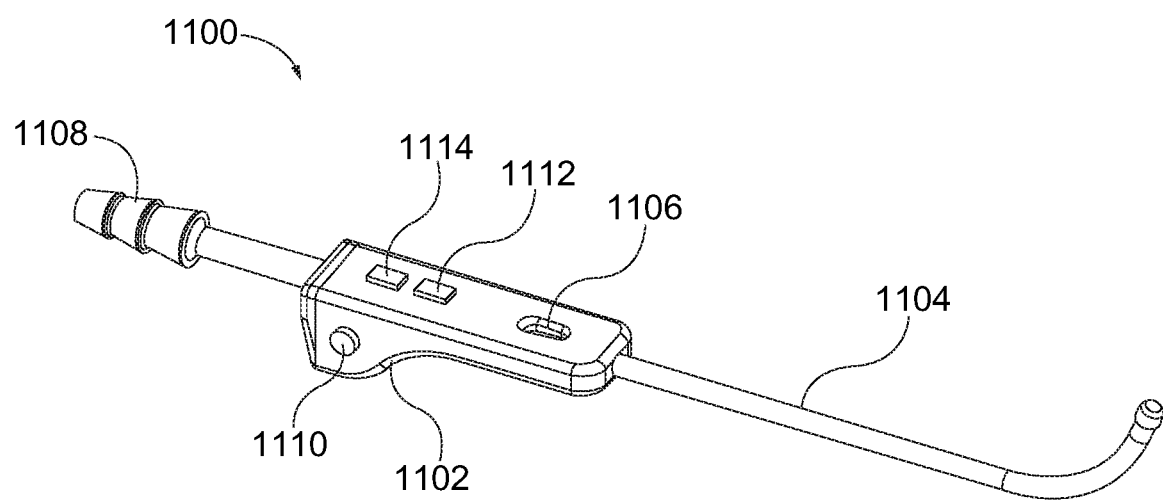
FIG. 18 depicts a perspective view of another exemplary suction instrument with a set of integrated controls.
Figure 19:
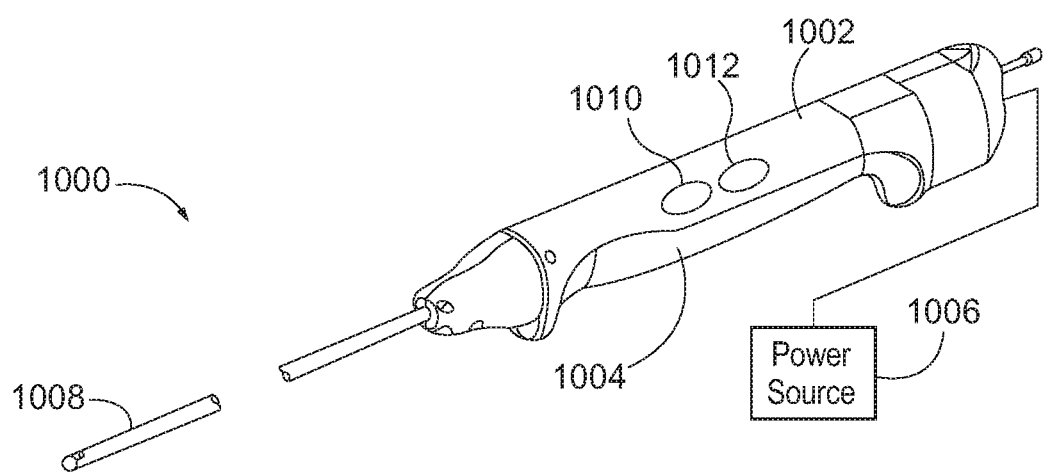
FIG. 19 depicts a perspective view of an exemplary surgical debriding instrument with a set of integrated controls.

FIGS. 18 and 19 show additional implementations of surgical instruments including integrated controls that may be configured to interact with a system such as the IGS navigation system (100). FIG. 18 shows a perspective view of an exemplary suction instrument (1100), having similar function to previously discussed suction instruments (e.g., the suction instrument (602) of FIG. 14, the suction instrument (800) of FIG. 16, the suction instrument (900) of FIG. 17). The suction instrument (1100) includes a grip portion (1102), a suction cannula (1104), a control vent (1106), and a suction port (1108), each having a similar function as the corresponding components of previous examples. The suction instrument (1100) also includes a first button (1110), a second button (1112), and a third button (1114) disposed on the top and side of the grip portion (1102), with the internal components of such buttons being positioned within the grip portion (1102) such that they do not interfere with the internal suction path of the surgical instrument (1100) (e.g., a channel (not pictured) that runs from the suction port (1108), to the suction vent (1106), and then to the distal tip of the suction cannula (1104)).

FIG. 19 shows a perspective view of an exemplary debriding instrument (1000) having integrated IGS navigation controls. The debriding instrument (1000) may be operable during a surgical procedure to cut or shave bone, tissue, and other materials. A grip body (1002) contains electrical and mechanical components that may receive power from a connected power source (1006) in order to drive a cutting head (1008) which catches tissue and other materials between an inner rotating cutting edge and an outer static cutting edge in order to cut or shave the affected material. As an example, the debriding instrument (1000) may incorporate any of the teachings of U.S. patent application Ser. No. 16/012,922, entitled "Surgical Shaver with Feature to Detect Window State" filed Jun. 20, 2018, now abandoned, the disclosure of which is incorporated by reference herein; and/or U.S. Patent App. No. 62/741,594, entitled "Hollow Tube Surgical Instrument with Single Axis Sensor," filed Oct. 5, 2018, the disclosure of which is incorporated by reference herein. The grip body (1002) also includes a handgrip (1004), as well as a first button (1010) and a second button (1012), positioned on the grip body (1002) and near the handgrip (1004), so that they may be accessible while holding the debriding instrument (1000) during use.

With references to the suction instrument (1100), the first button (1110), the second button (1112), and the third button (1114) may be used singularly, or in combination with each other to provide a variety of unique inputs that can be interpreted by the IGS navigation system (100) software or other software or devices of the IGS navigation system (100) to provide control, as has been previously described. With reference to the debriding instrument (1000), the first button (1010) and the second button (1012) may be used singularly, or in combination with each other to provide a variety of unique inputs that can be interpreted by the IGS navigation system (100) software or other software or devices of the IGS navigation system (100) to provide control, as has been previously described. While described and shown herein as a press-button, it should be understood that any of the buttons disclosed herein may instead be a rocker switch, slide switch, or other switch, a rotatable knob, pad, or other element, or other similar mechanical input.

For each instrument, inputs may be provided to the IGS navigation system (100) via a wireless connection (e.g., Bluetooth, Wi-Fi), or a wired connection (e.g., a data transmission via a physical connection such as a navigational guidewire capable of transmitting a signal from the suction instrument (1100) to the coupling unit (132) or another device). As another example, the debriding instrument (1000) may be in communication with the IGS navigation system (100) via the connection to the power source (1006) or another attached device; and may provide inputs to the IGS navigation system (100) via that connection.

For each instrument, reusability factors may be considered when implementing integral controls, which may include sealing such controls so that they are resistant to contamination with tissue, bacteria, or other materials, providing controls that may be sterilized during a sterilization procedure without damage, and other similar techniques as described herein, and as will be apparent to one of ordinary skill in the art in light of this disclosure.

It should also be understood that the number, types, and positions of controls show in FIGS. 18 and 19 are exemplary and, while they provide advantages in terms of functionality and accessibility to a user during use of the associated instrument, other variations exist. For example, the suction instrument (1100) may include one or more proximity controls (e.g., such as the proximity control (812) or the proximity control cluster (912)) instead of or in addition to any of the shown buttons. Similarly, the debriding instrument (1000) may include proximity controls (e.g., such as the proximity control (812) or the proximity control cluster (912)), navigation wheels (e.g., such as the navigation wheels (410, 430)), control overlays (e.g., such as the control overlay (500) or the control clip (1200)), and other control features instead of or in addition to any of the shown buttons.

F. Integration Module for Image Guided Surgery Navigation

Figure 20:
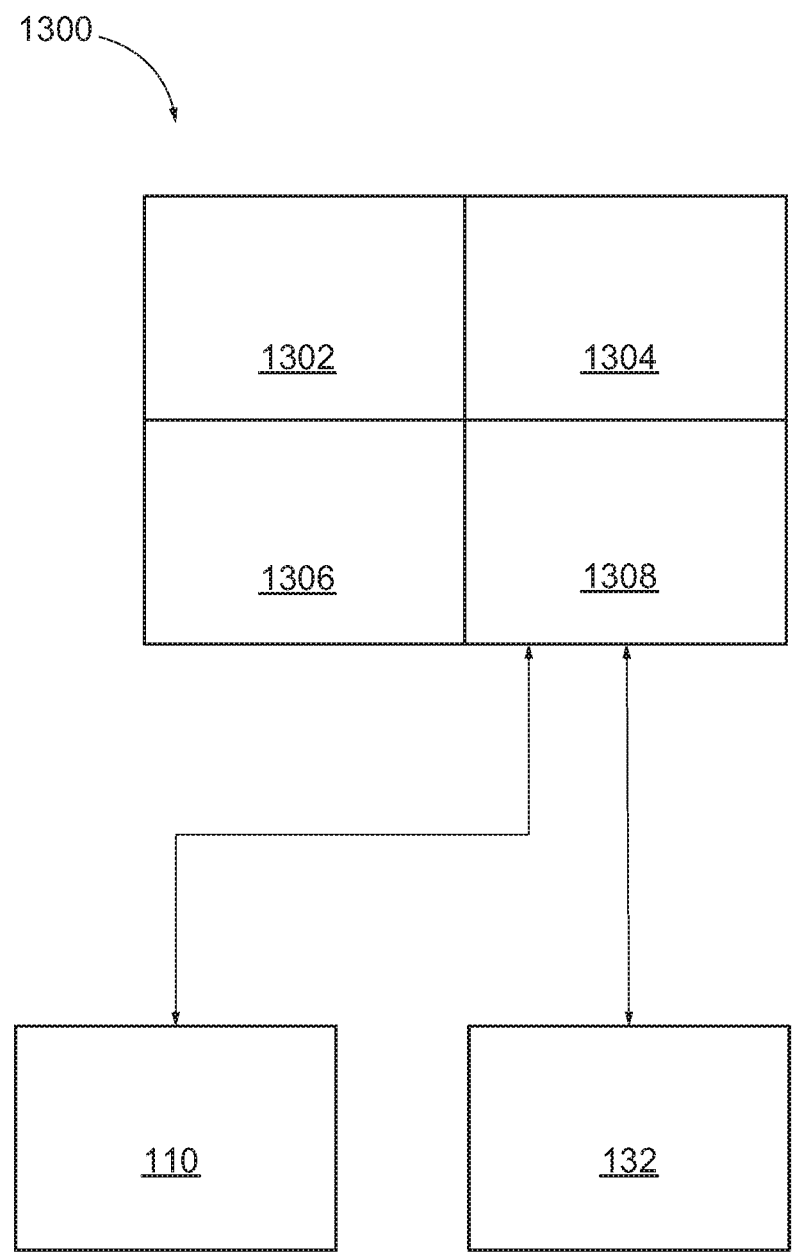
FIG. 20 depicts a schematic diagram of an exemplary integration module that a surgical instrument may be configured with to provide control during IGS navigation.

FIG. 20 shows a schematic view of an exemplary integration module (1300) that may be integrated into a surgical instrument such as those shown in at least FIGS. 3, 11-13, and 16-20 to provide integration features with a system such as the IGS navigation system (100). Such integration may include using one or more of the disclosed controls for changing the view of an IGS navigation software or interface displayed on the display screen (114), activating a device or device feature on a surgical instrument being used with the IGS navigation system (100), changing a configuration of a device or software in use with the IGS navigation system (100), and other features.

The integration module (1300) of this example includes a control interface (1302) that may be coupled with one or more controls (e.g., buttons, navigation wheels, proximity controls) to receive user inputs provided via those controls as electronic signals. The integration module (1300) also includes a processor (e.g., a microprocessor, logic circuit, or other electronic circuit) (1304) that may include or be paired with a memory (e.g., an electronic storage), and that may receive signals via the control interface (1302) so that they may be analyzed, processed, stored, acted upon, or transmitted to another device. Received signals may be provided to the IGS navigation system (100) as they are received, or may be modified, encoded, converted, or compressed by the processor (1304) prior to transmission, such as where three discrete signals are received via the control interface (1302) indicating that three separate buttons (e.g., the first button (1208), the second button (1210), and the third button (1212)) are being pressed, and may be converted into one or more different signals indicating a particular combination of pressed buttons.

The processor (1304) may also operate a communication device (1308) in order to transmit received inputs to another device or system, such as the processor (110), the coupling unit (132), or both, or another system or device of the IGS navigation system (100). The communication device (1308) may be a wireless (e.g., Bluetooth, Wi-Fi) or wired (e.g., USB, data-over-power, or other data connection) connection as has been described above in the context of each of the various the types of integral controls disclosed herein. This may include, for example, a low-energy Bluetooth transceiver, Wi-Fi transceiver, or other wireless component. In some implementations, the function of the communication device (1308) may be performed partially or entirely by the coupling unit (132), such as where the coupling unit (132) receives inputs directly from the control interface (1302) and then transmits them to the processor (110).

The integration module (1300) may also include a power source (1306), which may be a one-time use battery, rechargeable battery, or wired power source (e.g., power via USB) as may be desirable for a particular implementation. For example, a device that is intended to be disposed after one or several uses may include a one-time use battery as the power source (1306), while devices that are intended to be sterilized and reused more than several times may include the power source (1306) as a rechargeable battery, replaceable battery, or a connection via USB to a pre-existing source of power on or connected to the associated surgical instrument (e.g., the power source (1006)).

The integration module (1300) may be implemented in different ways, and may be, for example, a single board computer or module having varying form factor and capabilities suitable for a particular application. For example, an integration module for the control overlay (500) may need to be small enough to be compartmentalized on the surface of the overlay; or may need to be curved to fit within the body. As another example, an integration module for the suction instrument (1100) may need to be designed with a hole or channel on its surface so that the suction path is not blocked, interrupted, or diverted. As yet another example, an integration module for the control clip (1200) may need to be split across several components or boards that may be stacked within the control module (1202). Other ways in which the features of the integration module (1300) may be formed, packaged, or integrated with one or more of the examples disclosed herein exist and will be apparent to one of ordinary skill in the art based on the disclosure herein.

IV. Method for Input Pattern Configuration and Detection

As has been previously discussed with reference integral controls such as those shown in at least FIGS. 3, 11-13, and 16-20, inputs received by those devices and communicated to the IGS navigation system (100) may be received or interpreted as a variety of commands, from basic system commands (e.g., moving a mouse cursor or pressing an enter button or space bar) to more complex software specific commands (e.g., setting and recalling a pre-set perspective or viewpoint within an IGS navigation application). Such commands may either be provided by the integral control to the IGS navigation system (100) in a form that can be used directly by the IGS navigation system (100); or may be provided in a form that can be interpreted or otherwise converted by the IGS navigation system (100) prior to use. As an example, a rapid series of inputs may be received via a control such as the proximity control cluster (912), and the IGS navigation system (100) may have to parse that series of inputs to determine if they are discrete inputs (e.g., independent and unrelated movements of the mouse cursor) or if they are a pattern associated with activating a more complex action (e.g., recalling the view or perspective to a pre-set location and orientation).

Figure 21:
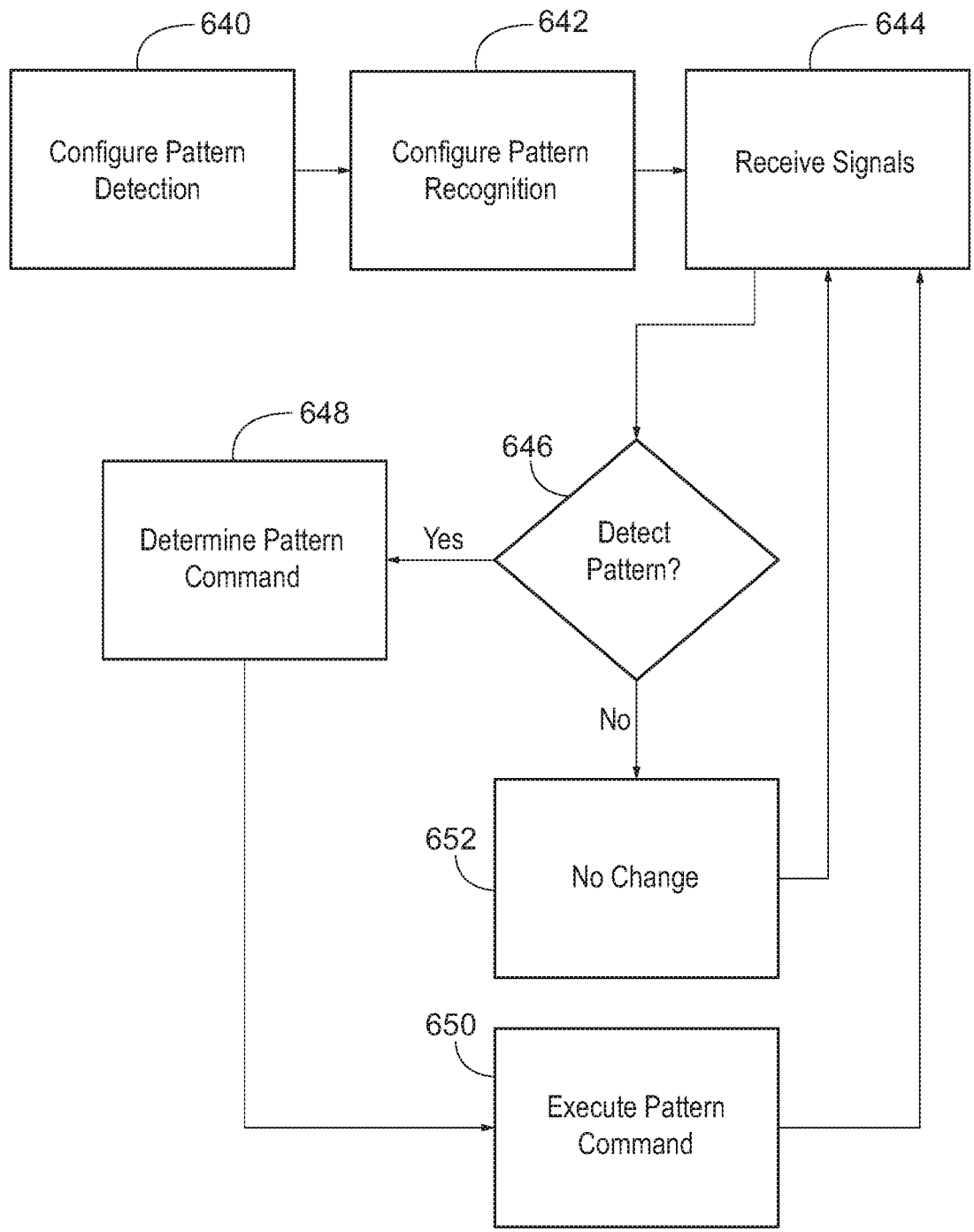
FIG. 21 depicts a set of steps that may be performed by a configured device to detect, identify, and react to inputs from one or more proximity sensors.

FIG. 21 depicts a set of steps that may be performed by a configured device such as the IGS navigation system (100) to detect, identify, and react to inputs from one or integral controls, such as the proximity control (812), the proximity control cluster (912), the control overlay (500), or the navigation wheels (410, 430). Initially, pattern detection may be configured for a device (block 640), which includes configuring what types of patterns the device is able to receive via one or more controls. As an example, this can be thought of as creating a mapping table having a single column, where each row of the column is a unique input. In the case of the proximity control (812), this could include a row for a single tap, a row for a double tap, a row for a triple tap, a row for each of swiping across the proximity control (812) up, down, left, and right, a long press, a short press, and other unique inputs. Next, pattern recognition may be configured (block 642) for the device, which includes configuring what types of actions the IGS navigation system (100) performs when a detectable pattern is recognized. This can be thought of as creating a second column in the earlier mapping table and assigning a reaction or task with each unique and detectable input. The result is similar to a key-value pairing, where each unique input is a key, and each resulting action is a value associated with that.

With pattern detection and recognition configured, the IGS navigation system (100) may then receive (block 644) signals from one or more integral controls during a procedure in which it is being used. This could include receiving signals via a physical connection or wirelessly, from the communication module (450), the control overlay (500), or the port (810, 910) as a user of one of those devices interacts with the device. As the signals are received (block 644), the IGS navigation system (100) will analyze them and attempt to detect (block 646) one or more patterns that have been configured (block 640). This could include, for example, comparing the received (block 644) signals to a data structure such as the earlier discussed mapping table to determine if a pattern contained therein has been defined. Where a pattern is detected (block 646), the IGS navigation system (100) will determine (block 648) a reaction or task associated with that pattern (e.g., by checking the value for that key in the mapping table) and then execute (block 650) that reaction or task.

If no pattern is detected (block 646) within an individual set of signals, or if a pattern is detected (block 646) and after an associated task is executed (block 650), the IGS navigation system (100) will continue to receive (block 644) additional signals and detect (block 646) patterns contained therein. Variations on the above method for interpreting and acting upon configurable inputs exist and will be apparent to one skilled in the art in light of this disclosure.

V. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A medical device comprising: (a) a medical procedure feature, wherein the medical procedure feature is configured to interact with an anatomical structure of a patient; (b) a handle body adapted to be gripped by a user, wherein the medical procedure feature is distal to the handle body; (c) a set of controls positioned on the handle body and configured to provide inputs to an input controller when the set of controls are interacted with by the user; and (d) a communication module that is operable to communicate with an image guided surgery (IGS) navigation system; wherein the input controller is configured to receive a set of inputs from the set of controls and provide the set of inputs to the IGS navigation system; and wherein the set of inputs is configured to cause the IGS navigation system to modify the perspective of an IGS application running on the IGS navigation system.

Example 2

The medical device of Example 1 wherein the set of controls comprises a first navigation wheel and a second navigation wheel, wherein the first navigation wheel is oriented perpendicularly to the second navigation wheel.

Example 3

The medical device of Example 2, wherein the set of inputs comprises a horizontal movement received from a rotation of the first navigation wheel, and a vertical movement received from a rotation of the second navigation wheel, and wherein the IGS navigation system is configured to move a cursor horizontally in response to the horizontal movement of the first navigation wheel and the IGS navigation system is configured to move the cursor vertically in response to the vertical movement of the second navigation wheel.

Example 4

The medical device of any one or more of Examples 2 through 3, wherein the set of controls further comprises a first button that is activated by depressing the first navigation wheel, and a second button that is activated by depressing the second navigation wheel.

Example 5

The medical device of Example 4, wherein the set of inputs comprises a single input received from interaction with one of the set of controls, and a combined input received from simultaneous interaction two or more of the set of controls.

Example 6

The medical device of Example 5, wherein the set of inputs is configured to cause the IGS navigation system to move and rotate the perspective of an IGS application with six degrees of freedom.

Example 7

The medical device of any one or more of Examples 1 through 6, wherein the set of inputs comprises a navigation wheel, and wherein the navigation wheel comprises a set of spokes, each spoke having a first conductive face connected to an electrical supply with a first voltage, each spoke further having a second conductive face connected to an electrical supply with a second voltage.

Example 8

The medical device of Example 7, wherein the navigation wheel further comprises a conductive switch positioned to contact the first conductive face when the navigation wheel rotates in a first direction, wherein the conductive switch is further positioned to contact the second conductive face when the navigation wheel rotates in a second direction, and wherein the input controller is configured to determine the direction and speed of rotation of the navigation wheel based upon a set of voltages contacting the conductive switch during rotation.

Example 9

The medical device of any one or more of Examples 7 through 8, wherein the navigation wheel further comprises a shaft having a first conductive portion that supplies the first voltage to the first conductive face, and a second conductive portion that supplies the second voltage to the second conductive face.

Example 10

The medical device of any one or more of Examples 8 through 9, wherein the conductive switch comprises a flexible conductive pin.

Example 11

The medical device of any one or more of Examples 1 through 10, wherein the set of controls comprises a navigation wheel, and wherein the navigation wheel is adapted to be fully exposed to sterilant during a sterilization procedure.

Example 12

The medical device of any one or more of Examples 1 through 11, wherein: the medical procedure feature is a guidewire; and the communication device is a wireless transceiver.

Example 13

The medical device of any one or more of Examples 1 through 12, wherein the medical procedure feature comprises a guide catheter and a dilation catheter slidably received by the guide catheter.

Example 14

The medical device of any one or more of Examples 1 through 13, wherein the handle body comprises a proximal end and a distal end, wherein the set of controls are positioned at the distal end, proximal to the medical procedure feature.

Example 15

The medical device of any one or more of Examples 1 through 14, wherein the IGS navigation system includes a display screen configured to provide different cross-sectional views of a patient's head, wherein the input controller is configured to change cross-sectional views of a patient's head displayed via the display screen in response to inputs provided via the set of controls positioned on the handle body.

Example 16

A control overlay comprising: a body portion; a communication module that is operable to communicate with an image guided surgery (IGS) navigation system; and a set of controls positioned on the body portion and configured to provide inputs to an input controller when the set of controls are interacted with by a user; wherein: the input controller is configured to receive a set of inputs from the set of controls and provide the set of inputs to the IGS navigation system; the set of inputs is configured to cause the IGS navigation system to modify the perspective of an IGS application running on the IGS navigation system; and the body portion is adapted to fit against a handle body of a medical instrument.

Example 17

The control overlay of Example 16, wherein the set of controls comprises a pointing stick and a set of buttons.

Example 18

The control overlay of any one or more of Examples 16 through 17, further comprising a first cutout and a second cutout positioned along the body portion so that, when the body portion is fit against the handle body of the medical instrument, a set of inner finger-grips of the medical instrument pass through the cutouts.

Example 19

The control overlay of any one or more of Examples 16 through 18, wherein the control overlay is adapted to attach to the handle body using one or more of: a friction fit; an adhesive; a mechanical catch; and a magnetic mount.

Example 20

A method for providing user input to an image guided surgery (IGS) navigation system comprising the steps: fitting a control overlay to a medical instrument; pairing the control overlay with an IGS navigation system; receiving, at an input controller of the control overlay, a set of user inputs via a set of controls positioned on the control overlay; providing the set of user inputs to the IGS navigation system; wherein the set of user inputs are configured to cause the IGS navigation system to modify the perspective of an IGS application running on the IGS navigation system.

Example 21

The medical device of any one or more of Examples 1 through 15, wherein the set of controls comprises a proximity control positioned within a portion of the handle body, wherein the proximity control is configured to detect the presence of an object proximate to an outwardly facing portion of the proximity control, wherein the proximity control is further configured to provide inputs to the input controller based upon the presence of the object.

Example 22

The medical device of any one or more of Examples 13 through 15, or 21, wherein the medical procedure feature comprises a suction cannula that is operable for suctioning material through a channel, wherein the proximity control is positioned outside of the channel, wherein the communication module comprises a port configured to couple the medical device with the IGS navigation system and provide the medical device with power and communication of data.

Example 23

The medical device of any one or more of Examples 13 through 15, or 21 through 22, wherein the proximity control comprises a cover on the outwardly facing portion, wherein the cover is configured to seal the proximity control and the portion of the handle body and prevent contaminants or liquids from entering, wherein the cover is further configured to allow the passage of light through the cover.

Example 24

The control overlay of Example 16, wherein the set of controls comprises a proximity control, wherein the proximity control is configured to detect the presence of an object proximate to an outwardly facing portion of the proximity control, wherein the proximity control is further configured to provide inputs to the input controller based upon the presence of the object.

Example 25

A medical device comprising: a medical procedure feature, wherein the medical procedure feature is configured to interact with an anatomical structure of a patient; a handle body adapted to be gripped by a user, wherein the medical procedure feature is distal to the handle body; an integration module comprising a control interface and a processor; a set of controls positioned on the handle body and configured to provide inputs to the control interface when the set of controls are interacted with by the user; and a communication device that is operable to communicate with an image guided surgery (IGS) navigation system; wherein the processor is configured to: receive a set of inputs via the control interface, wherein the set of inputs describes a combination and pattern of user interactions with the set of controls, identify an input based on the set of inputs, and determine whether the input is a device input or a navigation input, where the input is a device input, modify the operation of the medical procedure feature, and where the input is a navigation input, provide the input to the IGS navigation system, wherein the input is configured to modify the operation of an IGS navigation software being executed by the IGS navigation system.

Example 26

The medical device of Example 25, wherein the set of controls comprises a control selected from the group consisting of: a navigation wheel, a button, a proximity control, a knob, and a pointing stick.

Example 27

The medical device of any one or more of Examples 25 through 26, wherein the medical procedure feature comprises a suction cannula that is operable for suctioning material through a channel, wherein the set of controls and the integration module are positioned outside of the channel.

Example 28

The medical device of Example 27, wherein the set of controls comprises: a first button and a second button positioned on a top surface of the handle body, and a third button positioned on a side surface of the handle body.

Example 29

The medical device of any one or more of Examples 27 through 28, wherein the integration module comprises the communication device, and wherein the communication device is configured to wirelessly transmit the input to the IGS navigation system.

Example 30

The medical device of any one or more of Examples 25 through 28, wherein the medical procedure feature comprises a cutting head that is operable to rotate an inner cutting edge to cut or shave material trapped against an outer cutting edge, wherein the integration module is within the handle body.

Example 31

The medical device of Example 30, wherein the set of controls comprises a first button and a second button positioned on a side surface of the handle body.

Example 32

The medical device of any one or more of Examples 30 through 31, wherein the communication device is configured to transmit the input to the IGS navigation system via a connection configured to provide the medical device with power from a power source.

Example 33

The medical device of any one or more of Examples 25 through 32, further comprising a position sensing coil configured to produce position signals based on the position of the position sensing coil within an electromagnetic field, wherein the communication device comprises a coupling unit, and wherein the processor is further configured to provide the input to the IGS navigation system via the coupling unit.

Example 34

The medical device of any one or more of Examples 25 through 33, wherein the handle body is sealed to prevent exposure of the integration module to liquids during sterilization of the medical device.

Example 35

The medical device of any one or more of Examples 25 through 34, wherein the medical procedure feature comprises a suction cannula that is operable for suctioning material through a channel of the medical device when an external vacuum source provides suction via the channel, and wherein the input is configured to cause the external vacuum source to provide suction via the channel.

Example 36

The medical device of Example 35, wherein the suction cannula that is operable for providing irrigation via the channel when an external irrigation source provides irrigation via the channel, and wherein the input is configured to cause the external irrigation source to provide irrigation via the channel.

Example 37

A control comprising: a control body shaped to fit on a portion of a medical device; an integration module comprising a control interface, a processor, and a communication device, wherein the communication device is operable to communicate with an image guided surgery (IGS) navigation system; and a set of controls positioned on the control body and configured to provide inputs to the control interface when the set of controls are interacted with by a user; wherein the processor is configured to: receive a set of inputs via the control interface, wherein the set of inputs describes a combination and pattern of user interactions with the set of controls, identify an input based on the set of inputs, and determine whether the input is a navigation input, where the input is a navigation input, provide the input to the IGS navigation system, wherein the input is configured to modify the operation of an IGS navigation software being executed by the IGS navigation system.

Example 38

The control of Example 37, wherein the processor is further configured to: determine whether the input is a device input; where the input is a device input, provide the input to the IGS navigation system, wherein the input is configured to modify the operation of a medical device in use with the IGS navigation system.

Example 39

The control of any one or more of Examples 37 through 38, wherein the control body comprises: a device saddle; a first clamp arm extending from the device saddle; a second clamp arm extending from the device saddle opposite the first clamp arm; and a control module positioned on the first clamp arm, wherein: the set of controls are positioned on the control module, the integration module is positioned within the control module, and the first clamp arm and the second clamp arm fit opposite sides of the portion of the medical device.

Example 40

The control of Example 39, wherein the device saddle is shaped to fit a grip portion of a dilation catheter slider when the first clamp arm and the second clamp arm are fit on opposite sides of the dilation catheter slider.

Example 41

The control of Example 40, wherein the first clamp arm and the second clamp arm are flexibly biased towards each other.

Example 42

The control of Example 41, wherein an interior side of each of the first clamp arm and the second clamp arm comprise an attachment feature adapted to increase the force necessary to remove the control body from the dilation catheter slider.

Example 43

The control of any one or more of Examples 37 through 42, further comprising a disposable battery configured to provide power to the control interface, the processor, and the communication device.

Example 44

A method for providing user input to an image guided surgery (IGS) navigation system comprising the steps: fitting a control clip on a grip portion of a dilation catheter slider, wherein the control clip comprises a device saddle shaped to fit against the grip portion, and a set of clamp arms shaped to grip opposite sides of the dilation catheter slider; pairing a communication device of the control clip with an IGS navigation system; receiving, at a control interface of the control clip, a set of user inputs via a set of controls positioned on the control clip, wherein the set of inputs describes a combination and pattern of user interactions with the set of controls; identifying an input based on the set of inputs, and determining whether the input is a navigation input; where the input is a navigation input, providing the input to the IGS navigation system; wherein the input is configured to modify the operation of an IGS navigation software being executed by the IGS navigation system.

VI. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/ replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one skilled in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A method for providing user input from a medical device to an image guided surgery (IGS) navigation system, wherein the medical device includes a handle body, wherein the handle body includes a set of controls, wherein the set of controls includes at least first and second controls, the method comprising:
    (a) receiving, at a control interface, a set of inputs when each of first and second controls are interacted with by a user, wherein the set of inputs describes a combination and pattern of user interactions with each of the first and second controls of the set of controls;
    (b) identifying an input based on the set of inputs, and determining whether the input is a device input or a navigation input using a processor;
    (c) if the input is a device input, then relaying information regarding operation of a medical procedure feature of the medical device; and
    (d) if the input is a navigation input, then implementing the input on the IGS navigation system to modify operation of an IGS navigation software being executed by the IGS navigation system.

2. The method of claim 1, wherein the act of implementing further comprises changing a view of the IGS navigation software or an interface displayed on a display screen.

3. The method of claim 1, further comprising parsing the set of inputs to determine whether the set of inputs are separate and discrete inputs or the set of inputs describe the combination and pattern of user interactions with each of the first and second controls.

4. The method of claim 1, further comprising interpreting the set of inputs using a mapping table that includes at least one column.

5. The method of claim 1, further comprising wirelessly transmitting the navigational input to the IGS navigation system.

6. The method of claim 1, wherein the navigational input is interpreted or converted by the IGS navigation system prior to modifying the operation of the IGS navigation software.

7. The method of claim 1, further comprising the user manually gripping the handle body of the medical device.

8. The method of claim 1, wherein the first and second controls each include at least one of a navigation wheel, a button, a proximity control, a knob, or a pointing stick, the method further comprising manually actuating the navigation wheel, the button, the proximity control, the knob, or the pointing stick.

9. The method of claim 1, wherein the first control includes a first button, wherein the second control includes a second button, wherein the act of receiving further comprises receiving the set of inputs when of each of the first and second buttons positioned on the handle body of the medical device are interacted with by the user, wherein the set of inputs describes a combination and pattern of user interactions with each of the first and second buttons.

10. The method of claim 1, wherein the first control includes a first navigation wheel, wherein the second control includes a second navigation wheel, wherein the act of receiving further comprises receiving the set of inputs when of each of the first and second navigation wheels positioned on the handle body of the medical device are interacted with by the user, wherein the set of inputs describes a combination and pattern of user interactions with each of the first and second navigation wheels.

11. The method of claim 1, wherein the first control includes a first proximity sensor positioned on the handle body and the second control includes a second proximity sensor positioned on the handle body, wherein the act of receiving further comprises sensing motions or movements of an object within a detectable distance above the first and second proximity sensors.

12. The method of claim 1, further comprising removably coupling the first and second controls of the set of controls with the handle body of the medical device.

13. The method of claim 12, the act of removably coupling further comprising:
   (a) fitting a control clip on a grip portion of a dilation catheter slider of the medical device, wherein the control clip comprises a device saddle shaped to fit against the grip portion; and
   (b) pairing a communication device of the control clip with the IGS navigation system.

14. The method of claim 1, wherein the medical procedure feature comprises a suction cannula, the method further comprising suctioning material through a channel of the suction cannula, wherein the set of controls are positioned outside of the channel.

15. A method for providing user input from a medical device to an image guided surgery (IGS) navigation system, wherein the medical device includes a handle body, wherein the handle body includes a proximity device, the method comprising:
   (a) receiving, at a control interface, a set of inputs when the proximity device is interacted with by a user, wherein the set of inputs describes a combination and pattern of user interactions with the proximity device;
   (b) identifying an input based on the set of inputs, and determining whether the input is a device input or a navigation input using a processor;
   (c) if the input is a device input, then relaying information regarding operation of a medical procedure feature of the medical device; and
   (d) if the input is a navigation input, then implementing the input on the IGS navigation system to modify operation of an IGS navigation software being executed by the IGS navigation system.

16. The method of claim 15, wherein the proximity device includes at least one proximity sensor, wherein the act of receiving further comprises receiving the set of inputs as motions or movements of a target within a detectable distance from the at least one proximity sensor that is positioned on the handle body.

17. The method of claim 15, wherein the set of inputs includes one or more swipes across the proximity device in different directions, wherein the act of implementing modifies at least one of control a mouse pointer, rotation a view or image, or scroll along a view or image.

18. The method of claim 15, wherein the proximity device includes a proximity control cluster, wherein the set of inputs comprises:
   (a) a scrolling motion across the proximity control cluster to cause a view or a perspective to scroll, rotate, or zoom, or
   (b) a clockwise or a counter-clockwise rotational motion around a perimeter of the proximity control cluster to cause a view or a perspective to rotate or zoom.

19. A method for providing user input from a medical device to an image guided surgery (IGS) navigation system, the method comprising:
   (a) fitting a control clip on a grip portion of a dilation catheter slider of the medical device;
   (b) pairing a communication device of the control clip with the IGS navigation system;
   (c) receiving, at a control interface of the control clip, a set of user inputs via a set of controls positioned on the control clip, wherein the set of inputs describes a combination and pattern of user interactions with the set of controls;
   (d) identifying an input based on the set of inputs, and determining whether the input is a navigation input; and
   (e) if the input is a navigation input, then implementing the input on the IGS navigation system to modify operation of an IGS navigation software being executed by the IGS navigation system.

20. The method of claim 19, wherein the control clip comprises a device saddle shaped to fit against the grip portion, and a set of clamp arms shaped to grip opposite sides of the dilation catheter slider.

* * * * *